US009241954B2

(12) United States Patent
Ovejero Guisasola et al.

(10) Patent No.: US 9,241,954 B2
(45) Date of Patent: Jan. 26, 2016

(54) LIPOPOLYSACCHARIDE OF OCHROBACTRUM INTERMEDIUM AND THEIR USE AS IMMUNOSTIMULANT OF MAMMALIANS

(75) Inventors: Juan Ignacio Ovejero Guisasola, León (ES); Manuel Fresno Escudero, León (ES)

(73) Assignee: LABORATORIOS OVEJERO, S.A. (ES)

( * ) Notice: Subject to any disclaimer, the term of this patent is extended or adjusted under 35 U.S.C. 154(b) by 103 days.

(21) Appl. No.: 13/375,174

(22) PCT Filed: Dec. 31, 2009

(86) PCT No.: PCT/EP2009/009342
§ 371 (c)(1),
(2), (4) Date: Dec. 29, 2011

(87) PCT Pub. No.: WO2010/139352
PCT Pub. Date: Dec. 9, 2010

(65) Prior Publication Data
US 2012/0107352 A1    May 3, 2012

(30) Foreign Application Priority Data
Jun. 4, 2009    (ES) .................................. 200930265

(51) Int. Cl.
| | |
|---|---|
| *A61K 39/00* | (2006.01) |
| *A61K 39/02* | (2006.01) |
| *A61K 39/38* | (2006.01) |
| *C12N 1/00* | (2006.01) |
| *C12N 1/12* | (2006.01) |
| *A61K 31/739* | (2006.01) |
| *A61K 39/39* | (2006.01) |

(52) U.S. Cl.
CPC ............... *A61K 31/739* (2013.01); *A61K 39/39* (2013.01); *A61K 2039/55572* (2013.01)

(58) Field of Classification Search
CPC ....... A61K 35/74; A61K 38/00; A61K 39/00; A61K 39/02; A61K 47/00; A61K 2039/6018; A61K 2039/6031; A61K 2039/6087; A61K 2300/00; A61K 2236/00; A61K 2039/555572; C12P 19/02; C12P 19/44; C12P 19/64; C07K 14/195; C07K 14/23
See application file for complete search history.

(56) References Cited

PUBLICATIONS

Velasco et al. Carbohydrate Research, Pergamon, GB, vol. 306, No. 1-2, Jan. 1, 1998, pp. 283-290.*
Velasco et al., (International J of Systematic Bacteriology. 1998. vol. 48 pp. 759-768).*
Velasco, 1997 et al., ( Clin. and Diag. Lab. Immunol.1997. vol. 4(3): 279-284).*
Alonso-Urmeneta et al., (Clin Diag Lab Immunol. 1998vol. 5(66):749-754).*
Cieslak, T. J., et al. "Pyogenic infections due to Ochrobactrum anthropi", *Clin. Infect. Dis.* 22, 1996, pp. 845-847.
(Continued)

*Primary Examiner* — Ja'na Hines
(74) *Attorney, Agent, or Firm* — Ginger R. Dreger; Arnold & Porter LLP

(57) ABSTRACT

The present invention relates to the isolation, purification and characterization of the Lipopolysaccharide (LPS) from *Ochrobactrum intermedium* strain LMG3306, and their use as immunostimulant of mammalians, the process for the preparation of a pharmaceutical compound for the treatment and/or prevention of the sepsis and adjuvant for a vaccine in immunosupressed animals and against *Leishmania*.

4 Claims, 29 Drawing Sheets

(56) References Cited

PUBLICATIONS

Fresno, M. et al., "Cytokines and infectious diseases", *Immunol Today* vol. 18, No. 2, 1997, 3 pgs.

Hoffman, E. et al., "TLR-targeted therapeutics", *Nature Reviews Drug Discovery* vol. 4, Nov. 2005, pp. 879-880.

Kwissa, M, et al., "The science of adjuvants", *Expert Vaccine Rev.*, 6(5), 2007, pp. 673-684.

Netea, M. G., et al., "Does the shape of lipid A determine the interaction of LPS with Toll-like receptors?" *Trends Immunol.* vol. 3. No. 23, Mar. 2002, pp. 135-139.

Rictschcl, E. T., et al. "Bacterial endotoxins:chemical structure, biological activity and role in septicaemia", *Scand. J. Infect. Dis. Suppl.* 31, 1982, pp. 8-21.

Velasco et al., "Determination of the O-specific polysaccharide structure in the lipopolysaccharide of *Ochrobactrum anthropi* LMG 3331", *Carbohydrate Research* 287, 1996, pp. 123-126.

Velasco et al., "Structural studies on the lipopolysaccharide from a rough strain of *Ochrobactrum anthropi* containing a 2,3-diamin-2,3-dideoxy-d-glucose disaccharide lipid A backbone", *Carbohydrate Research* 306, 1998, pp. 283-290.

Velasco et al., "Evaluation of the relatedness of *Brucell* spp. and *Ochrobactrum anthropi* and description of *Ochrobactrum intermedium* sp. nov., a new species with a closer relationship to *Brucella* spp.", *Int'l Journal of Systematic Bacteriology*: 48, 1998, pp. 759-768.

Velasco et al., "*Brucella abortus* and Its Closest Phylogenetic Relative, *Ochrobactrum* spp., Differ in Outer Membrane Permeability and Cationic Peptide Resistance", *Infection and Immunity*, Jun. 2000, pp. 3210-3218.

Zahringer, U., et al. "The lipopolysaccharide of Legionella pneumophila serogroup 1 (strain Philadelphia 1): chemical structure and biological significance", *Prog. Clin. Biol. Res.* 392, 1995, pp. 113-139.

\* cited by examiner

MURINE CUTANEOUS LEISHMANIOSIS
*Protective immunity depends on the induction of T cells producing Th1 cytokines*
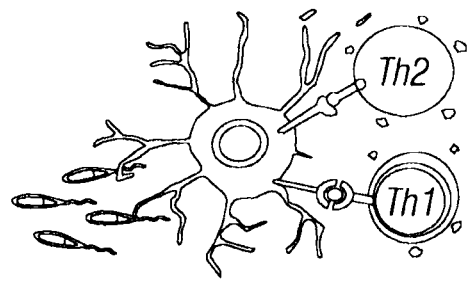
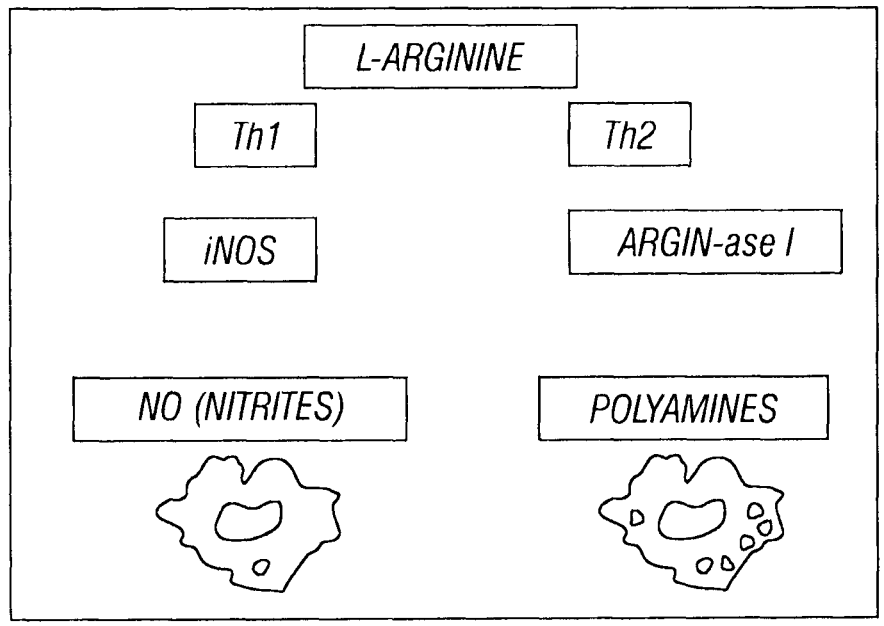
FIG. 5

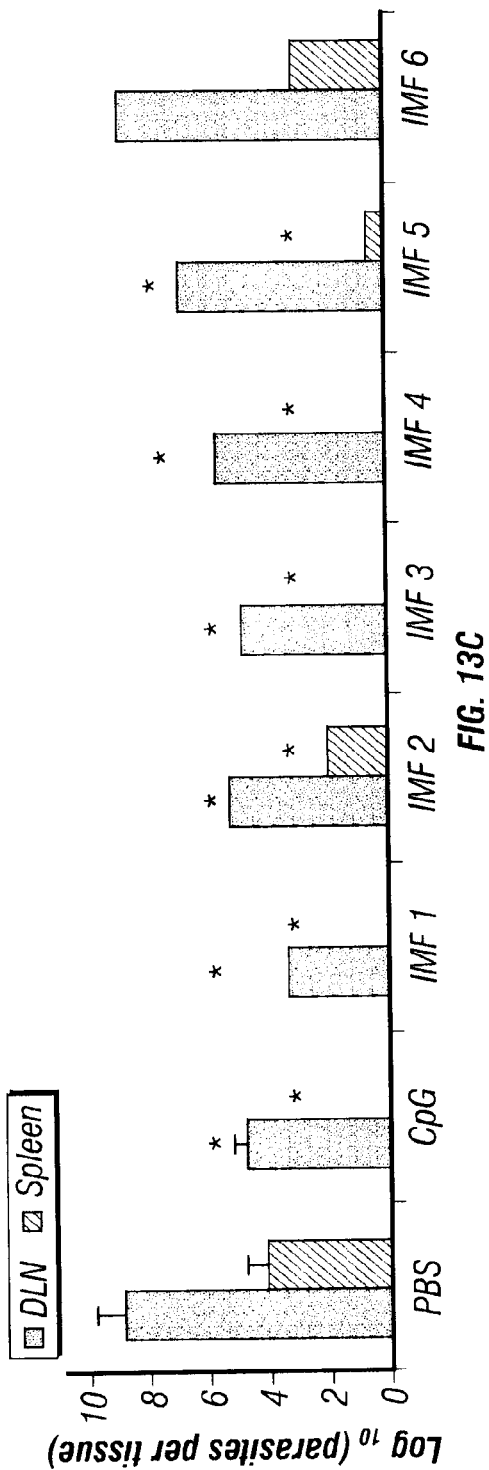

LIPOPOLYSACCHARIDE OF OCHROBACTRUM INTERMEDIUM AND THEIR USE AS IMMUNOSTIMULANT OF MAMMALIANS

CROSS-REFERENCE TO RELATED APPLICATIONS

This application is a National Stage Application under 35 U.S.C. 371 of International Application No. PCT/EP2009/009342 filed Dec. 31, 2009, the contents of which is incorporated herein by reference in its entirety.

The present invention relates to the isolation, purification and characterization of the Lipopolysaccharide (LPS) from *Ochrobactrum intermedium* strain LMG3306, and their use as immunostimulant of mammalians, the process for the preparation of a pharmaceutical compound for the treatment and/or prevention of the sepsis and adjuvant for a vaccine in immunosupressed animals and against *Leishmania*.

BACKGROUND ART

The members of the genus *Ochrobactrum* are included in the alpha-2 subgroup of the domain Proteobacteria. They are primarily soil dwellers known to be pathogenic only in critically ill or immunocompromised patients or in patients with indwelling catheters. Although in such situations *Ochrobactrum* can cause meningitis, osteomyelitis, bacteraemia, and septicaemia, these bacteria are unable to establish chronic infections by themselves and are cleared from normal hosts after catheter removal (Cieslak, T. J., C. J. Drabick, and M. L. Robb. 1996. *Pyogenic infections due to Ochrobactrum anthropi*. Clin. Infect. Dis. 22:845-847.)

Since the composition of all lip polysaccharides, main component of outer membrane of gram-negative bacteria follows a general principle, which includes a polysaccharide attached to a lipid component termed lipid A through a specific sugar called 2-keto-3-deoxyoctulosonic acid (KDO) (Rietschel, E. T., Schade, U., Jensen, M., Wollenweber, H. W., Luderitz, O. and Greisman, S. G. 1982. *Bacterial endotoxins: chemical structure, biological activity and role in septicaemia*. Scand. J. Infect. Dis. Suppl. 3:8), it has been assumed that all LPS molecules have identical biological effects.

However, this concept has been modified by studies showing great variance in the capacity of several LPS species to produce cytokine synthesis, this effect being related to the structural features of their lipid A portion (Netea, M. G., van Deuren, M., Kullberg, B. J., Cavaillon, J. M. and van der Meer, J. W. M. 2002. *Does the shape of lipid A determine the interaction of LPS with Toll-like receptors? Trends Immunol*. 23:135.).

*Legionella pneumophila*, a Gram-negative facultative intracellular bacteria, is also similar to *Brucella* as regards both low endotoxicity and chemical structure of its LPS and significantly lower than that elicited by enterobacterial LPS (Zahringer, U., Knirel, Y. A., Lindner, B., Helbig, J. H., Sonesson, A., Marre, R. and Rietschel, E. T. 1995. *The lipopolysaccharide of Legionella pneumophila serogroup 1 (strain Philadelphia 1): chemical structure and biological significance*. Prog. Clin. Biol. Res. 392:113. 26).

*Ochrobactrum anthropi* is the closest known relative of brucellae (Velasco et al. *International Journal of Systematic Bacteriology* 48 (1998) 759-768). Despite their close phylogenetic relatedness, *B. abortus* and *Ochrobactrum* differ markedly in OM properties and that these wide differences are caused at least in part by little changes in the LPS (Velasco et al. *Infection and Immunity* 68 (2000) 3210-3218)

The complete core-lipid A backbone of the LPS from *Ochrobactrum intermedium* LMG 3301 and the O-chain from *Ochrobactrum anthropi* LMG 3331 LPS was determined (Velasco et al. *Carbohydrates Research* 306 (1996) 123-126; Velasco et al. *Carbohydrates Research* 306 (1998) 283-290; Velasco et al. *Infection and Immunity* 68 (2000) 3210-3218).

The strain of *Ochrobactrum intermedium* LMG 3306 was described by Velasco et al. (*International Journal of Systematic Bacteriology* 48 (1998) 759-768) and nevertheless, no LPS from *Ochrobactrum intermedium* LMG 3306 have been described previously.

On the other hand, Approximately 900,000 cases of sepsis occur annually only in the United States, causing roughly 210,000 deaths and costing almost 17 billion dollar. Sepsis is a common disease with rising incidence and a mortality ranging from 27-48%. Septic shock is a consequence, frequently lethal of sepsis. The overwhelming inflammation that occurs along with infection during sepsis has been the target of several therapeutic interventions. Despite, the inflammatory aspects of sepsis more that 20 years of clinical trials with general anti-inflammatory agents have shown that this approach was not overly successful.

The pathological mechanisms leading to sepsis are complex and far from being understood. Sepsis involves a systemic inflammatory response followed by a compensatory anti-inflammatory response. The balance between them is crucial for host survive. Moreover, animal models of sepsis do not easily mimic this complex nature of sepsis in human patients.

Recently, there have been some attempts to treat those effects by Toll-like receptor (TLR) antagonists since it is believed that most of the consequences of the septic shock are due to huge release of circulating endotoxin (LPS). Thus, Eritoran, a structural analogue of lipid A portion of LPS which acts as TLR4 antagonist is in phase II and showed a reduction in mortality in severe sepsis patients In addition, TAK-242 is a TLR4 signal transduction inhibitor that decrease proinflammatory cytokine levels and also decrease mortality in a subgroup of severe sepsis patients with high IL-6 levels.

Nowadays, there are many infections diseases for which there is no vaccine available. In some of these cases the failure is due to the lack of the correct adjuvant to induce the correct and appropriate immune response—For some infections agents, as intracellular bacteria, viruses and most protozoans, the protective immune response is of the T helper 1 type (TH1) characterized by IFN-gamma production. In contrast, protective response against most helminths is of the type 2 (TH2), characterized by IL-4 production (Fresno, M., M. Kopf, and L. Rivas. 1997. Cytokines and infectious diseases. Immunol Today 18:56-58). Few adjuvants, are available for human vaccines formulation, due to the toxicity of many of them, due to an exarcebated Th1 induction. Alum, which is really not an adjuvant, is used in most human vaccine formulations. Recently, agonist of Toll-like receptors (TLR) have attracted great interest (Hoffman, Nature Reviews Drug Discovery 4, 879, 2005) (Kwissa; Expert Vaccine Rev., 6, G73, 2007). Several antigens together with several agonists of various TLRs are currently being analyzed.

Finally, one of the major problems of any vaccine formulation, including those already licensed in that they rarely works in immunosuppresed subjects. Besides some of them have secondary effects on those patients (Kwissa, et al 2007).

The complete core-lipid A backbone of the wild deep-rough LPS (a LPS in which O-Chain is not present and lack some monosaccharides from the outer core part) from *Ochrobactrum intermedium* LMG 3301 was described by Velasco et al. Carbohydrates Research 306 (1998) 283-290; the O-chain from wild smooth LPS from *Ochrobactrum anthropi* LMG 3331 LPS was determined (Velasco et al. Carbohydrates Research 306 (1996) 123-126; and lipid A, and molecular weight of the complete LPS was published by Velasco et al. Infection and Immunity 68 (2000) 3210-3218.

The strain of *Ochrobactrum intermedium* LMG 3306 was described by Velasco et al. (International Journal of Systematic Bacteriology 48 (1998) 759-768) and nevertheless, no wild smooth LPS from *Ochrobactrum intermedium* LMG 3306 have been described previously.

SUMMARY OF THE INVENTION

Now, it has been demonstrated that the lipopolysaccharide of *Ochrobactrum intermedium* strain LMG 3306 (IM) is effective in the treatment and/or prevention of sepsis as well as adjuvant for vaccines in immunosupressed animals and against leishmaniasis.

Therefore, according to a first aspect of the present invention, it relates to the use of the lipopolysaccharide of *Ochrobactrum intermedium* strain LMG 3306 (IM) in the preparation of a medicament for the treatment and/or prevention of sepsis as well as adjuvant vaccine in immunosuppressed animals and against leishmaniasis.

According to an embodiment of the present invention, it provides the use of lipopolysaccharide of *Ochrobactrum intermedium* strain LMG 3306 (IM) in the preparation of a medicament for the treatment and/or prevention of septic shock and endotoxic shock.

According to another embodiment of the present invention, it provides the use of lipopolysaccharide of *Ochrobactrum intermedium* strain LMG 3306 (IM) as an adjuvant for vaccines for infectious diseases in both humans and animals.

According to a particular embodiment of the present invention, it provides the use of IM in the preparation of a medicament for the treatment and/or prevention of infections in animals, including human, that are immunosuppressed.

According to the present invention, the uses described in the lipopolysaccharide of *Ochrobactrum intermedium* strain LMG 3306 are applicable in both humans and animals. Thus, the reference to use in animals throughout the present invention also include human.

In summary the immunostimulant of mammalians, cures and prevents septicaemia and endotoxemia, has vaccine adjuvant properties in immunosuppresed animals and has vaccine adjuvant properties and a protective and curative effect on the experimental mouse model in footpad leishmaniasis.

The IM (Lipopolysaccharide from *Ochrobactrum intermedium* strain LMG3306) has been proved to have a broad activity as immunostimulant that includes:

Induce the production of IL-12 in macrophages.
The levels of TNF induced by the LPS of the invention are much lower than enteric LPS resulting in no pathological effect
The LPS of the present invention induces T helper 1 (TH1) activation and gamma-IFN production.

This compound has been related to the ability of stimulating an immune response in a mammal. Thus, the invention provides an immunostimulant composition comprising the *Ochrobactrum intermedium* strain LMG3306 Lipopolysaccharide and optionally one or more pharmaceutically acceptable excipients. Preferably, the modulation of the immune response consists in enhancing the immunocompetence of human beings.

The present invention relates to the use of the IM, immunostimulant of mammalians as a compound that prevents and cure septicaemia and endotoxemia. The invention particularly relates. with the use as adjuvant to improve the vaccination in normal and experimental immunosuppresed animals
In this regard, as an example of its adjuvant properties the present invention particularly relates to the use of the IM as a vaccine adjuvant for experimental lehismaniosis infection and a curative and protective effect cutaneous leishmaniosis using the experimental mouse model of the *Leishmania* major footpad leishmaniosis.

The present invention relates to process for the preparation of the LPS from *Ochrobactrum intermedium* strain LMG3306 as a compound to use in the medicine field as an immunostimulant of mammalians.

The invention provides a specific activity as immunostimulant in experimental field trails develop in cows, pigs, dairy milk cattle and mice:

Influence in the increase of neutralizing antibodies against IBR viruses after an specific vaccination combined with the present invention
Induction of Macrophage Differentiation
Induction of TNF in Macrophages
Induction of IL-12 in Macrophages
Induction of IFN-gamma production by spleen lymphocytes
Immunostimulant act via TLR4 and TLR2 receptors
Influence of stimulation of T cells in a dose-dependent manner Accordingly, the present invention relates to the ability of *Ochrobactrum intermedium* strain LMG3306 Lipopolysaccharide (LPS) to being capable of stimulating an immune response in a mammal. Thus, the invention provides an immunostimulant composition comprising the *Ochrobactrum intermedium* strain LMG3306 Lipopolysaccharide and optionally one or more pharmaceutically acceptable excipients. Preferably, the modulation of the immune response consists in enhancing the immunocompetence of the mammal.

The present invention also relates to methods of modulating the immune response in a mammal comprising administering *Ochrobactrum intermedium* strain LMG3306 LPS or the pharmaceutical composition containing it to the mammal. Therefore, the present invention also relates to the use of the immunostimulant composition in the preparation of a medicament for inducing general cellular immunity in a mammal. The present invention also relates to the use of the immunostimulant composition of the invention in the preparation of a medicament for the induction of macrophage differentiation, TNF production, IL-12 production, IFN-gamma production by spleen lymphocytes and activate virus specific CD8 and CD4 T-cells, in an mammal comprising administering the LPS of *O. intermedium* LMG3306 to the mammal.

According to another embodiment, the immunostimulant composition of the invention is used as adjuvant for vaccines for better immunization against specific viruses and or bacteria contained in the vaccine.

Most work related to the prevention of endotoxic shock by low sublethal doses of these or other less toxic LPS have shown that prior inoculation is required (Hatao, F., et al., The induction of super-resistance using synthetic lipopolysaccharide receptor agonist rescues fatal endotoxemia in rats without excessive immunosuppression. Shock 2005; 23 (4): 365-70.). The inventors have surprisingly found that the lipopolysaccharide of *Ochrobactrum intermedium* strain LMG 3306 did not require a prior desensitization period, and just the inoculation of lipopolysaccharide of *Ochrobactrum intermedium* strain LMG 3306 in conjunction with LPS protected the toxic effect.

Also, most of the published data found a relationship between them, the suppression of TNF in vitro or in cell lines and desensitizing effects in vivo (see, e.g., Lehner, M D, et al, Lipopolysaccharide and Highly Purified Lipoteichoic Acid Via Different Toll-Like Receptors Independent of Paracrine Mediators. 2,001. J. Immunol. 166: 5161-5167). However, the inventors have now shown that the lipopolysaccharide of *Ochrobactrum intermedium* strain LMG3306, although protect the action of LPS in vivo, does not decrease the secretion of TNF or IL-12 in macrophage lines nor in peritoneal macrophages or spleen cells. Preliminary results in vivo also suggest that the lipopolysaccharide of *Ochrobactrum intermedium* strain LMG 3306 (IM) is capable of drastically reducing TNF levels induced by LPS although it make it in some way. In any case, there is no direct relationship between levels of TNF and protection. These results are surprising.

Other hypotheses attribute the desensitizing effect of increased production of IL-10 or TGF-β (Randow, F. et al., Mechanism of endotoxin desensitization: involvement of 35 interleukin 10 and transforming growth factor beta. J. Exp. Med 1995. 181, 1887-1892). However, there seems not to be the case, due to the fact that IL-10 is hardly be induced in vitro by IM, in fact it seems that something inhibits the production of IL-10 (although it is not significant) in peritoneal macrophages or spleen cells and the levels of IL-10 induced by LPS are not significantly increased by IM except in the case of spleen cells from C57BL/6 mice.

Another interesting aspect is the ability of IM to modulate immune responses between pathogens. So, using a system of *Leishmania major* infection, it has emerged that the IM potentiates the action of an immunogenic *Leishmania* antigen extract, without it in a similar way to CpG. CpG is a known immunomodulator that, through their union with TLR9, enhances the Th1 response (which are protective against pathogens such as *Leishmania* and many others) and has been patented as an immunomodulator and vaccine adjuvant. However, IM does not alter the Th1/Th2 profile in vivo so as exacerbated as does CpG. This could indicate that the IM would be better CpG adjuvant in infections where both humoral (Th2) and cellular (Th1) have an important role in protection. It is perhaps more important to have demonstrate that not only induces a protective response but that the IM can induce protection directly, i.e., has a therapeutic effect on infection with *Leishmania*.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

BRIEF DESCRIPTION OF THE DRAWINGS

FIG. 5 shows the protective immunity against Leishmaniasis and general characteristics of the immune schema of the course of action. As shown in the figure, the interaction of parasites with macrophages produce an immune response which, if it is based predominantly by the Th1 lymphocyte activation, the response to the parasite is effective and successful, whilst if the response with Th2 is the representative the infection will be manifest.

FIGS. 13A-C: (A) shows the evolution of the lesion in animals vaccinated with IM. It quantifies the footpad swelling along the infection. (B) shows the macroscopic state of the footpad lesions of the vaccinated animals with IM compared with control group (PBS). There are included photos of one animal that pertains to control group, one animal vaccinated with CpG, and all six animals vaccinated with SLA-IM, within six weeks of infection. (C) shows the quantification of the number of parasites in the spleen and lymphoid nodes (DLN) after seven weeks.

FIG. 14 shows a comparative table between the PBS control sample, CPG and IM for IgG1 and IgG2a antibodies including the ratio between them.

DETAILED DESCRIPTION OF PARTICULAR EMBODIMENTS/EXAMPLES

Figure 1:
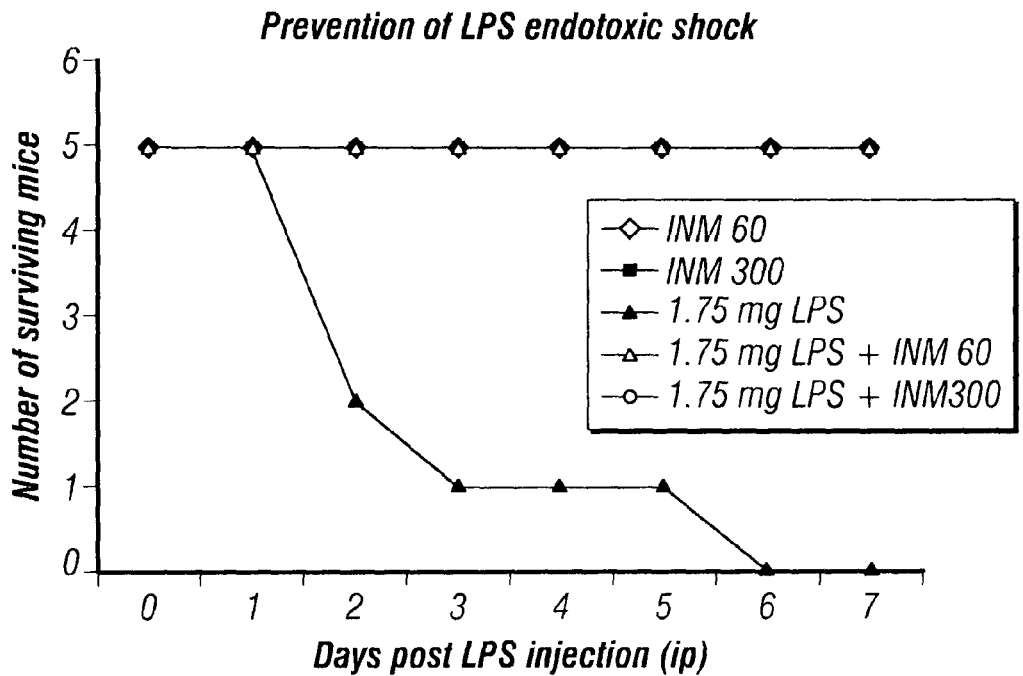
FIG. 1 shows the prevention of the toxic effect caused by LPS of *E. Coli* due to the use of IM. Groups of 5 mice were treated with LPS (1.75 mg) or IM (LPS of *Ochrobactrum intermedium*) 0.6 μg/Kg (dose 60) or 3 μg/Kg (dose 300) alone or in combination and survival evaluated.

The term "immunostimulant composition" is defined herein in a broad sense to refer to any type of biological agent in an administrable form capable of stimulating an immune response in a mammal inoculated with the product.

As used herein, the term "purified" as it relates to LPS indicates that the LPS has been subjected to fractionation or purification procedures, such as, but not limited to, those procedures disclosed above, to remove various other components, and which compositions substantially retains its expressed biological activity. Where the term "substantially purified" is used, this designation will refer to a composition in which the LPS form the major non-solvent component of the composition. For example, "substantially purified LPS" indicates that more than about 50%, about 60%, about 70%, about 80%, about 90%, about 95% of the non-solvent component of a solution or composition is the LPS of the present invention.

According to a preferred embodiment of the invention, the immunostimulant composition includes the LPS of $Ochrobactrum$ $intermedium$ strain LMG3306 in a substantially purified form wherein the non-solvent component is not contaminated with more than 0.2% of other compounds (DNA, RNA, Proteins, glucans, lipids . . . ).

An "immunologically effective amount" refers to an amount of an immunogenic sufficient to induce a detectable cellular or humoral immune response in a mammal.

A "protective immune response," as used herein, refers to a cellular or humoral immune response that prevents or delays infection or disease caused by a specified pathogen.

The compound of the invention may be prepared using conventional preparation techniques based on excipient, pH, and concentration According to an embodiment of the invention, the Lipopolysaccharide is extracted from $Ochrobactrum$ $intermedium$ LMG3306 following the steps:

a) centrifugate inactivated culture of $O.$ $intermedium$ LMG3306;

b) resuspend obtained sediment in saline suspension;

c) dialysis with purified water and polyethylene glycol;

d) precipitate with four volumes of methanol and 1% of saturated methanol with sodium acetate;

e) Freeze-dried to obtain crude LPS.

According to a preferred embodiment, once the crude LPS have been freeze-dried, it is purified following the steps:
1. dissolve crude LPS in buffer (10 mM Tris-HCl pH 7.5), optionally aided by ultrasound;
2. add proteinase K and incubate at room temperature;
3. collect the purified LPS by ultracentrifugation
4. freeze-dry the sample.

A more detailed description of a preferred embodiment of the manufacture process of the immunostimulant compound of the invention is represented in the following flow chart:

The manufacturing process comprises the following steps:

i) Defrost the Working Seed Bacteria (Strain LMG3306)

Preinoculum Preparation:
1. Prepare 1 l of Triptycase Soy Broth (TSB)
2. Prepare a tube with 60 ml of TSB
3. Take a pearl from the Working Seed frozen vial and include it in the tube with 60 ml of TSB.
4. Incubate at 37° C.±0.1 for 24 hours with shake.
5. Controls in the preinoculum: Identification and purity control: verify morphology of the colonies and microscopic morphology of the culture.

ii) Growth In Controls Fermentors

Inoculum Preparation
1. Prepare culture medium TSB supplemented with sucrose 2‰
2. Prepare a inoculation bottle with 5 l of TSB supplemented with sucrose 2‰ tempered and with a pH of 6.75±0.15.
3. Inoculate the preinoculum in an inoculation bottle with the culture medium.
4. Incubate at 37° C.±0.1 for 24 hours with shaking.
5. Controls in the inoculums: Identification and purity control: verify morphology of the colonies and microscopic morphology of the culture.

Culture
1. Clean and sterilize fermentors
2. Prepare 400 l of TSB supplemented with sucrose 2‰
3. Fill fermentors with 400 l of TSB supplemented with sucrose 2‰ adjust pH at 6.75±0.15.
4. Inject the inoculums in the fermentors with the culture medium.
5. Incubate at 37° C.±0.1 for 24 hours at a maximum shaker of 50 rpm
6. Controls of the culture: Identification and purity control: Verify morphology of the colonies and microscopic morphology of the culture.

Inactivation
1. Transfer culture to inactivation tank by sterile conductions.
2. Add formaldehyde solution until final concentration of 0.4%, and incubate at 37° C. with 10 rpm during 3 days Centrifugation
1. Connect the fermentors with the continuous centrifuge and centrifuged the content of the fermentors.
2. Bottle the inactivated culture in plastic bottles of 10 liters of capacity.
Keep at 4° C. until use.

iii) Follow the Method of Extraction LPS As Described Bellow

1-Centrifugation of inactivated culture of *Ochrobactrum intermedium* LMG 3306. The supernatant is removed.
2—Resuspend obtained sediment in saline suspension: 200 g/l 15 mM NaCl.
3—Add phenol in aqueous solution at 90% and 65° C.
4—Shake for 20' at 65° C. Cool the mixture until 10° C.
5—Centrifuge at 9000×g for 20'. Maintain at 4° C. for 24 hours.
6—Dialysis. First with purified water and then with polyethylene glycol
7—Precipitation with four volumes of methanol and with 1% of saturated methanol with sodium acetate.
8—Centrifugate at 9000×g during 20'. The supernatant is removed. Resuspend the extract with purified water and shake.
9—Repeat step 7.
10—Freeze-dried of the sample to obtain crude LPS.

iv) Purified LPS As According the Following Method

1. Dissolve 100 mg of crude LPS in 20 (5 mg/ml) of buffer (10 mM Tris-HCl pH 7.5) aided by ultrasound. Use 5-10 mg of LPS as controls.
2. Add 0.5 ml of proteinase K (50 μg/ml or 5 μg of proteinase per mg of LPS). Incubate at room temperature for 12 hours with stirring and gentle shaking.
3. Collect the purified LPS by ultracentrifugation (100.000×g, 6 hours). Resuspended the sediment in purified water.
4. Freeze-dry the sample.

v) Calculate the LPS Concentration to Prepare the Bulk Solution as Described Bellow Materials And Reagents
1. 1.25 N H2SO4: 6, 66 ml of commercial reagent in H2O DD to 100 ml.
2. 0.042 N periodic acid: 0.48 g of periodic acid (paraperiodic acid, H15IO6) in 100 ml of 0.125 N H2SO4.
3. 2% sodium arsenite in 0.5 N HCl (8.3 ml HCl concentrate to 200 ml H2O).
4. Thiobarbituric acid (Sigma): 0.3% pH 2 (dissolve in H2O DD at 50° C.). Use within 15 days.
5. Dimethyl Sulfoxide
6. Standards:
Kdo (Molecular Weight=255.1) (Sigma, store at −20° C.)
Deoxyxiribose (Molecular Weight=136) (Sigma, store at −20° C.)
7. LPS quantified from the previous batch
8. Glass tubes (cleaned with chromic mixture or equivalent), in which marbles fit.
9. Spectrophotometer Process
1. Prepare tubes with standards of Kdo (0.05 μg), deoxyribose (0.025 μg), LPS quantified from a previous batch (0.2 μg) and a blank reagent (200 μl H$_2$O).
  a) if the sample is LPS extracted and freeze-dried, weight 0.2 μg and prepare one tube
  b) if the sample is final product, prepare a tube with 200 μl. Add H2O in the tubes to 200 μl.
2. Place the tubes with the samples in ice, add 20 μl of 1.25 N H$_2$SO$_4$ in each tube and boil them covered with marbles for 20 minutes exactly. Cool them in ice. This step is not carried out with the standard ones.

3. Add 0.25 ml of periodic acid to samples and standards quickly, shake and incubate them at room temperature for 20 minutes (counting since the first tube). To add the periodic acid, tubes have to be in the same order than $H_2SO_4$ has been added. Hydrolysis time has to be optimized, because the quantity of Kdo measured depends on the solubilization of Kdo, but also on its degradation in the hydrolysis conditions (20 minutes are adequate for the *Ochrobactrum intermedium* LMG3306 LPS).

4. With the tubes in the same order as in 3, add 0.5 ml of sodium arsenite, shake in the vortex and wait 2 minutes, since the addition at the first tube (yellow colour that appears adding the reagent has to disappear in this time).

5. Add 2 ml of thiobarbituric acid to each tube quickly, in the same order as before. Boil them with marbles for 20 minutes.

6. Add 1 ml of DMSO exactly (avoids turbidity appearance) to each tube before cool them in a tray with tap water.

7. Incubate for 30 minutes at room temperature. Turn on the spectrophotometer at the beginning of the 30 minutes to stabilize the lamp.

8. Read each tube at 552 nm and at 536 nm (maximum absorption of Kdo and the deoxyribose, respectively). Plastic trays can be used.

Calculations

Mk552=Abs552/µmolk; calculate Mk536, Md552 y Md536 in the same way.

$$\mu\text{mol } KDO = \frac{Md536 \; Abs552 - Md552 \; Abs536}{M552 \; Md536 - Mk536 \; Md552}$$

k: KDO; d: deoxyribose; Abs: absorbance vi) Homogeneity of the Batch Until Final Process as Described Bellow This homogeneity validation of the quantification process is used twice during product manufacturing and according to the EMEA/CVMP/598/99 "Note for guidance on process validation":

At the end of the LPS extraction from the *Ochrobactrum intermedium* LMG 3306 inactivated culture, to know its richness.

In the final product to check the quantity of LPS.

The validated process is the one applied at the end of the extraction period. The quantities used in the analytical method are much higher than the ones quantified in the final product. With this method is pretended to know the concentration of the extracted LPS.

LPS quantification is carried out from one of its components quantification, Kdo. Kdo is a part of the LPS molecule and is always in constant amount for a specific LPS, but in variable amount in the different bacteria LPS. In *Ochrobactrum intermedium* LMG 3306 are 2 molecule of Kdo for each LPS molecule.

The quantification is carried out by spectrophotometry.

Quantification method of Kdo is not specific when the sample is extracted LPS, since any residual deoxyribose, (DNA component) left at the end of the extraction and purification process of the LPS, may interfere with the assay due to absorbance at the maximum absorbance wave length of Kdo (552 nm).

Validation of the quantification of Kdo using standard Kdo will demonstrate that Kdo is quantified linearly, precisely and accurately. The lack of specificity of the method when LPS sample is contaminated with deoxyribose rests is solved applying a correction formula. This formula adjusts the theoretical Kdo value obtained to the real value eliminating the deoxyribose interference where this interference exists in the sample.

Linearity of the deoxyribose quantification will show that this component behaves linearly not only alone but also when as a contaminant of LPS.

Each time this method is used, samples with different concentrations of standard Kdo, samples with different concentrations of deoxyribose, samples with different concentrations of LPS quantified previously and samples with different concentrations test sample will be used and all them will be measured at the deoxyribose maximum absorbance wave length (552 nm).

With the results obtained the following steps will be carried out:

A standard straight line with the standard Kdo: linearity is tested.

A standard straight line with the standard deoxyribose: linearity is tested.

A straight line with LPS quantified previously. Method is checked. Linearity is tested.

Quotients amongst absorbance values obtained for each sample are calculated, being the numerator the absorbance at 552 nm for the standard Kdo, for the LPS quantified previously and for the test samples and the absorbance at 536 nm for the standard deoxyribose.

To apply the formula, concentration values of the test samples which values of the quotients are nearest to the ones obtained from concentrations of standard Kdo and standard deoxyribose are taken, as long as selected values are inside standard straight line. If value is not inside the straight line the nearest value is taken instead.

The application of the formula determines Kdo micromoles in the test sample

The present invention further provides pharmaceutical compositions comprising the LPS immunostimulant compound provided herein in admixture with one or more pharmaceutically acceptable carriers or excipients. Suitable carriers will depend on the condition being treated along with the route of administration. It will be understood that pharmaceutical compositions of the invention may be used as adjuvants to increase an immune response to an antigen or enhance certain activities of cells of the immune system, or in some instances as a prophylactic or therapeutic composition to prevent or treat a particular condition in a subject.

Thus, in one embodiment, the present invention provides pharmaceutical compositions containing a LPS of the present invention and a pharmaceutically acceptable carrier, wherein the LPS is present in an amount effective to modulate an immune response, which is the amount of compound required to achieve the desired effect in terms of stimulating a desired immune response, treating or inhibiting a disease or condition. The pharmaceutical compositions can also act as an adjuvant when co-administered with an antigen.

The immunostimulant composition of the present invention exhibits strong immunostimulation effects when administered over a wide range of dosages and a wide range of ratios. According to a preferred embodiment, the immunostimulant composition comprises between 0.5 and 120 µg/ml LPS. More preferably, the composition comprises between 0.5 and 10 µg/ml LPS.

According to a preferred embodiment, the Lipopolysaccharide is in a homogeneous suspension in which the micellar phase is stable at 4° C. form more than 1 year period.

Preferably, the pH of the immunostimulant composition of the invention is between 2-12.

The amount of immunostimulant administered in conjunction with a vaccine dose is generally selected as an amount which together with the vaccine induces an immunoprotective response without significant adverse side effects in typical vaccines. Such amount will also vary depending upon which specific immunogens are employed and how they are presented. Generally, it is expected that each dose will comprise about 1-1000 μg of antigen and 0.1-200 μg of immunostimulant, most typically about 2-100 μg of antigen and 0.5-150 μg of immunostimulant, and preferably about 5-50 μg of antigen preparation and 1-75 μg of immunostimulant. Of course, the dosages administered may be dependent upon the age, weight, kind of concurrent treatment, if any, and nature of the antigen and immunostimulant being administered.

The mode of administration of the immunostimulant composition of the invention may be any suitable route which delivers a general immunostimulation. However, the immunostimulant composition is preferably administered parenterally via the intramuscular or subcutaneous routes. More preferably immunostimulant composition is administered subcutaneously. Other modes of administration may also be employed, where desired, thus examples of compositions of the invention include liquid preparations for orifice, e.g., oral, nasal, anal, vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions, the immunostimulant composition of the invention may be admixture with a suitable carrier, diluent, or excipient such as sterile water, physiological saline, glucose or the like.

The appropriate immunoprotection and non-toxic dose of such doses can be determined readily by those skilled in the art, i.e., the appropriate immunoprotective and non-toxic amount of the strain of this invention contained in the product of this invention may be in the range of the effective amounts of LPS. There is not minimum recommended age for application, indeed some studies carry out at 1 day are showed.

Of course, the administration can be repeated at suitable intervals if necessary. Preferably the application schedule is the following:

First Application 0.1 μg/Kg body weight (b. w.) by subcutaneous route.

Second Application at the same dosage 15 days after

More application: it is well recommended a 6 month-1 year application (0.1 μg/Kg b.w. Subcutaneous route).

EXAMPLE 1

Treatment And Prevention of Endotoxemia

For this, we use LPS from *E. coli* in acute model in Balb/c mice.

First, we determined the dose of *E. coli* LPS that induce 100% mortality in a 6 days period (lethal dose 100).

The LPS of *E. coli* strain O111: B4 was purchased from commercial house SIGMA (St. Louis, Mo., USA). In all studies, it is used phosphate-salt buffer as diluent of LPS. In all cases vehicle used was phosphate buffered saline (PBS). The appropriate dose of LPS for survival studies was determined by a dose response curve where increasing doses of LPS were administered to female BALB/c intraperitoneally (IP).

Prevention of the Lethal Effects of Endotoxemia

Female BALB/c mice undergoing endotoxemia were treated or not with 2 different doses of IM, 0.6 μg/Kg (dose 60) or 3 μg/Kg (dose 300), IP, 24 hr prior to LPS (*E. coli* O111: B4) challenge. LPS was injected IP at 1.75 mg/mouse.

To provide equal fluid resuscitation in the setting of sepsis, all injections were in the same volume.

IM at both doses completely prevented LPS associated death of the animals due to the endotoxic shock of the LPS of *E. coli*. Moreover, the IM-treated animals did not show any signs associated to septic shock (FIG. 1). The dose of LPS used was much higher than the dose of IM. Thus, it is unlikely that IM (LPS of *Ochrobactrum intermedium* 3306) may compete out LPS.

Cure of the Endotoxic Lethal Shock

Figure 2:
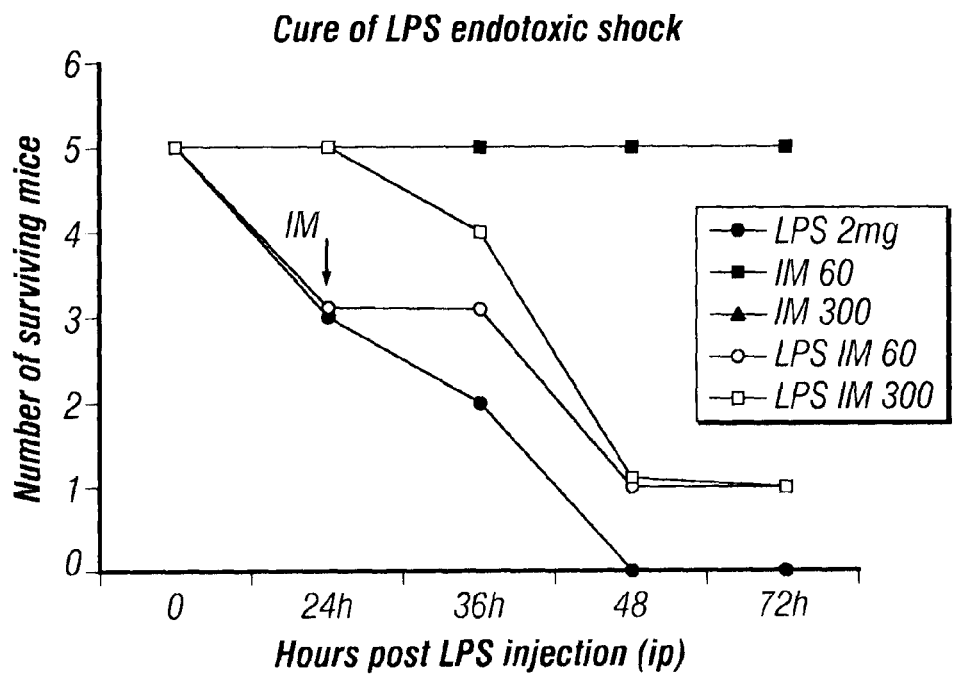
FIG. 2 shows the treatment of LPS endotoxic shock. Groups of 5 animals were treated with LPS (2 mg/animal). 24 hrs later they were injected with IM (LPS of *Ochrobactrum intermedium*) 0.6 μg/Kg (dose 60) or 3 μg/Kg (dose 300), and survival evaluated.

The main problem of sepsis is not usually to prevent it but rather to cure when the process starts. To test this, 5 mice were infected IP (intraperitoneally) with 2 mg/animal of LPS (*E. coli* O111: B4) and 24 hr later treated with LPS IM 0.6 μg/Kg (dose 60) or 3 μg/Kg (dose 300) IP. IM has protective effect on LPS induced mortality. Thus, at 72 hr after placebo treatment all animals die. However, IM treatment produced the survival of 20% of the animals and delayed their death significantly. This indicates that IM was able to partially cure mice undergoing endotoxic shock (FIG. 2).

Surprisingly IM-treated animals showed lower levels of blood clotting than in the placebo group. This fact is very important because the excessive clotting problems are associated with the phenomenon of sepsis and, in fact, the only compound recently approved for this condition has a blocking effect of coagulation.

Bacterial Peritonitis:

The lipopolysaccharide of *Ochrobactrum intermedium* LMG 3306 was tested in another model of sepsis, *E. coli* induced peritonitis induced sepsis.

Treatment of the *E. coli* Lethal Peritonitis:

For this study, female C57BU6 mice were inoculated with $10^7$ or $10^8$ live O26:B6 *E. coli* colony forming units (CFU) and 24 or 4 hours later respectively the animals were treated with LPS IM, 0.6 μg/Kg (dose 60) or 3 μg/Kg (dose 300), or placebo using a single IP injection.

Survival and pathological symptoms (anorexia, mortality, alopecia, choquexia, physical activity, etc. . . . ) were evaluated thereafter.

Twenty four hrs after *E. coli* injection some mice inoculated with $10^7$ CFU start to die (20% of them) and show pathological sign of sepsis (3 on averages in a scale of 0 to 5).

Figure 3:
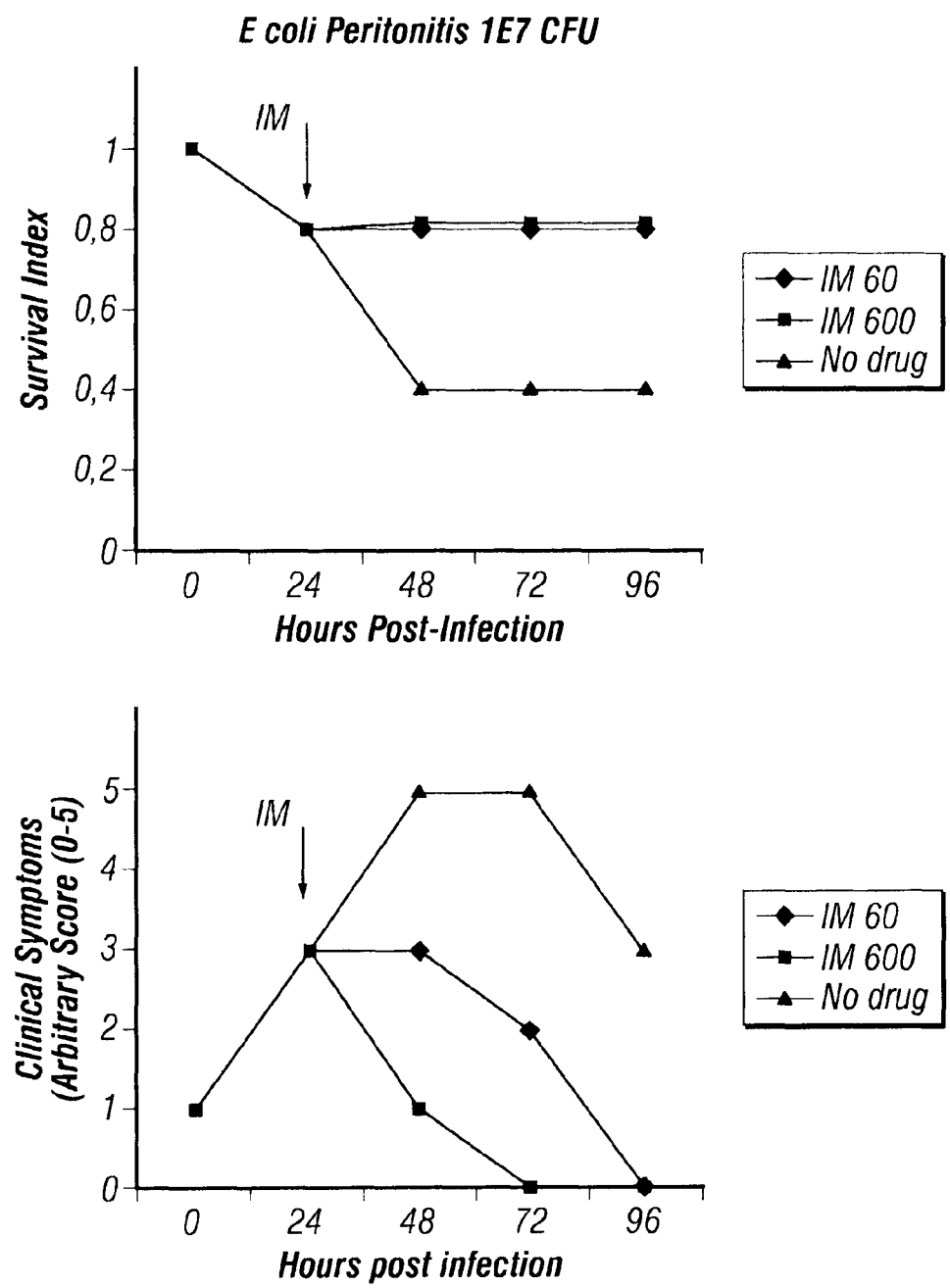
FIG. 3 shows the prevention of *E. Coli* peritonitis. Groups of 5 mice were infected with *E. Coli* (1E7 units for forming colonies, CFU); 24 hours after the animals were inoculated with IM (LPS of *Ochrobactrum intermedium*) 0.6 μg/Kg (dose 60) or 6 μg/Kg (dose 600), and survival evaluated (upper panel) and the clinical symptoms (inferior panel).

Treatment with IM prevented the death of animals and completely reversed, in a dose response manner, the pathological signs of sepsis (FIG. 3).

Figure 4:
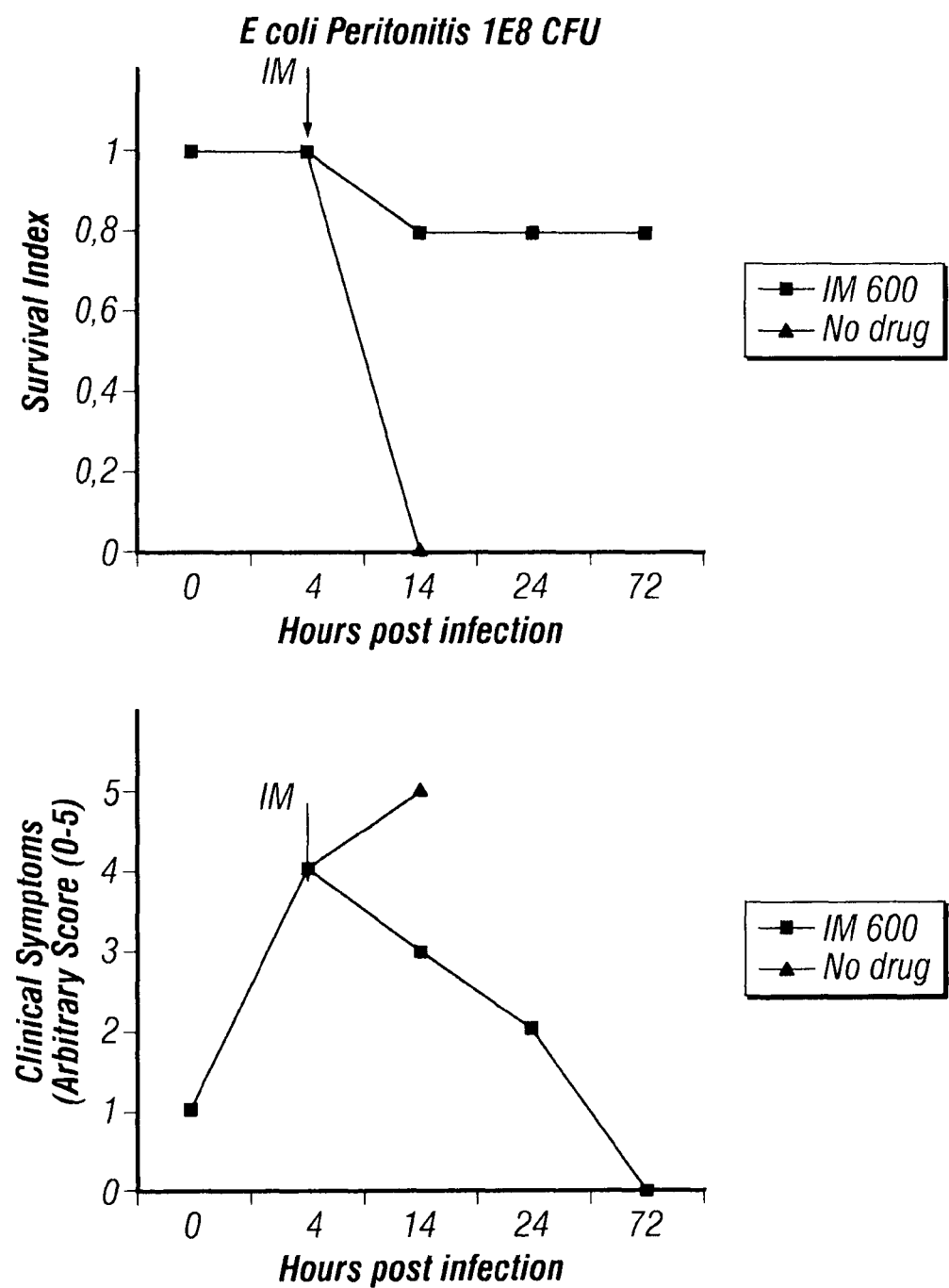
FIG. 4 shows the cure of *E. Coli* peritonitis. Groups of 5 mice were infected with *E. Coli* (1E8 units for forming colonies, CFU); 4 hours after, the animals were inoculated with IM (LPS of *Ochrobactrum intermedium*) 6 μg/Kg (dose 600), and survival evaluated (upper panel) and the clinical symptoms (inferior panel).

When the dose of $10^8$ CFU *E. coli* was used, all animals die at 24 hr; so they were treated with IM, 4 hrs after *E. coli* inoculation. At that time, no mice were dead, nonetheless, the average score of pathological symptoms was very high (4 out 5). At 14 hr all *E. coli*-infected mice were dead. Nonetheless, IM 3 μg/Kg (dose 300) prevented the dead of most of the animals (80% survival rate) and gradually decreased the severity of clinical symptoms (FIG. 4).

Adjuvant Effect In *Leishmania* Experimental Infection

Adjuvant Effect In the Footpad Infection:

It is well known that SLA (Soluble Antigen *Leishmania*) antigen extract does not induces a protective effect against experimental infection with *Leishmania major*, since this antigen is unable to activate the Th1 protective response (FIG. 5). But, when the SLA is combined with and adjuvant as CpG (U.S. Pat. No. 7,521,063) as adjuvant for vaccines due to stimulate the immune response via TLR9 and increase Th1 response) (Heeg, Int. J. Microbiol, 298, 33, 2008), is able via the TLR9 (Toll Like Receptor) to induce a protective Th1 (IFN-γ) activation (U.S. Pat. No. 6,890,542).

Thus, this model is very useful to test the IM in comparison with the well established use CPG as adjuvant for vaccination against experimental leishmaniosis.

Figure 6:
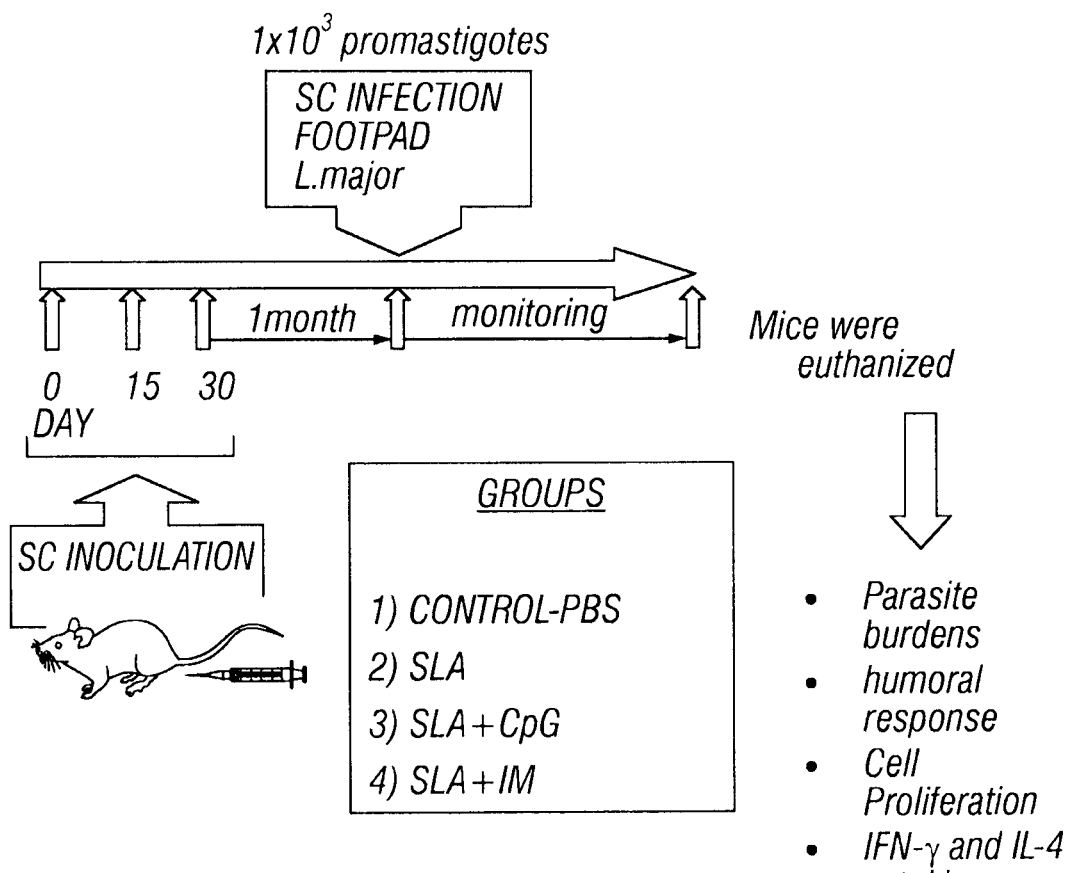
FIG. 6 shows the protocol of immunization to assess the potential adjuvant IM 25 (lipopolysaccharide of *Ochrobactrum intermedium* LMG 3306) in a vaccine against Leishmaniasis. Groups of 5 mice were vaccinated with SLA antigen alone or with CpG or IM at days 0, 15 and 30. On day 60, it is inoculated into each animal 1000 promastigotes in each footpad and assesses the evolution of the lesion and immune parameters.

In the FIG. 6 we show the protocol for this purpose.

Basically, SLA antigen is inoculated alone or together with CPG or with IM at day 0, 15 and 30.

Figure 7:
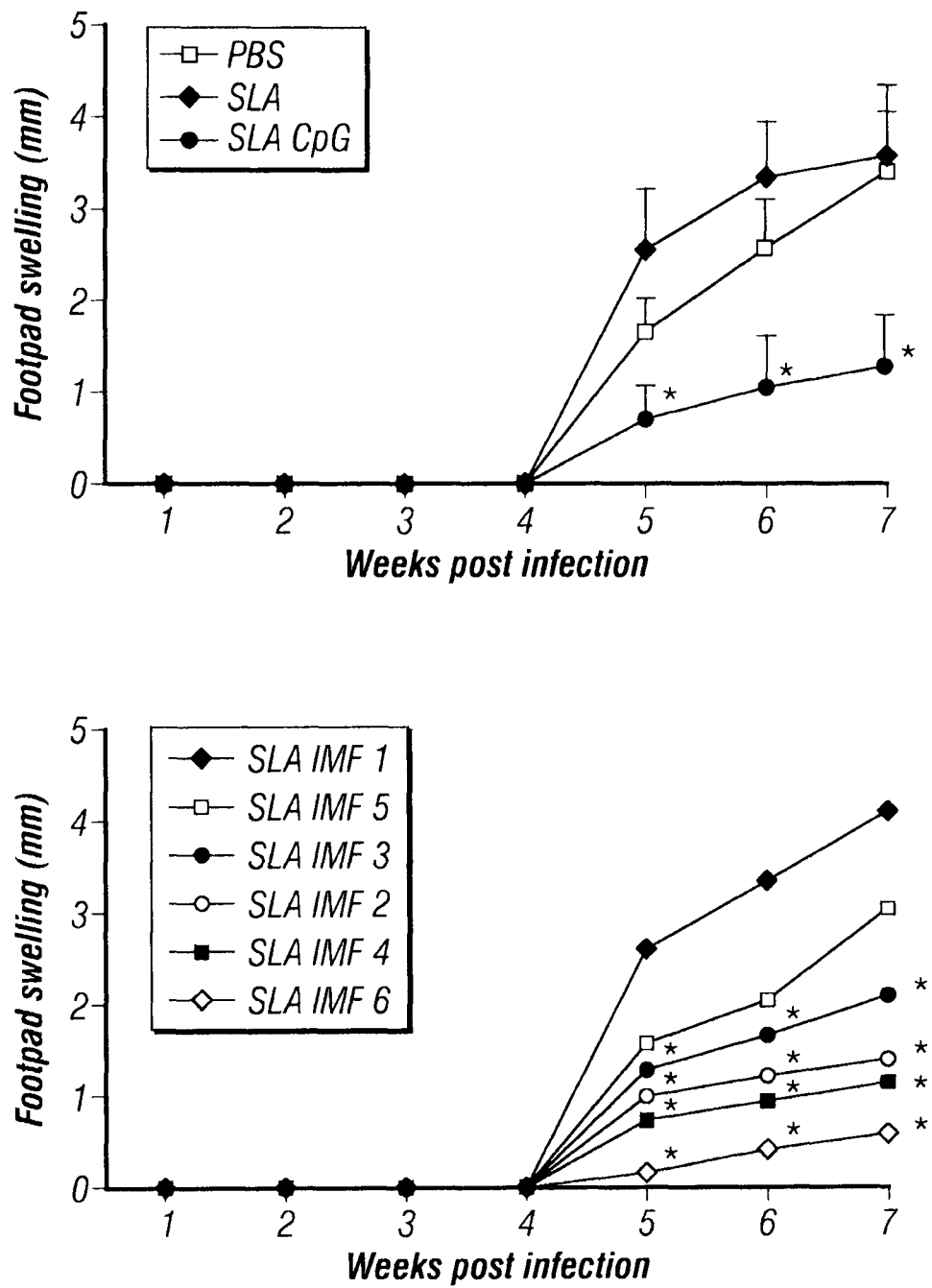
FIG. 7 shows the evolution of the lesion in animals vaccinated with SLA and SLA–CPG (top panel) or with SLA–IM as adjuvants. It quantifies the footpad swelling along the infection.

At day 60, 1,000 promastigotes are inoculated into each mice footpad and monitorized for lesions and immunological parameters. Evolution of infection could be macroscopically follow and correlates with number of parasites. As shown in FIG. 7, after inoculation it is patent the infection in the control group. SLA antigen does not produce any protective effect meanwhile both SLA+CPG and SLA+IM groups significantly reduce the lesions.

Figure 8:
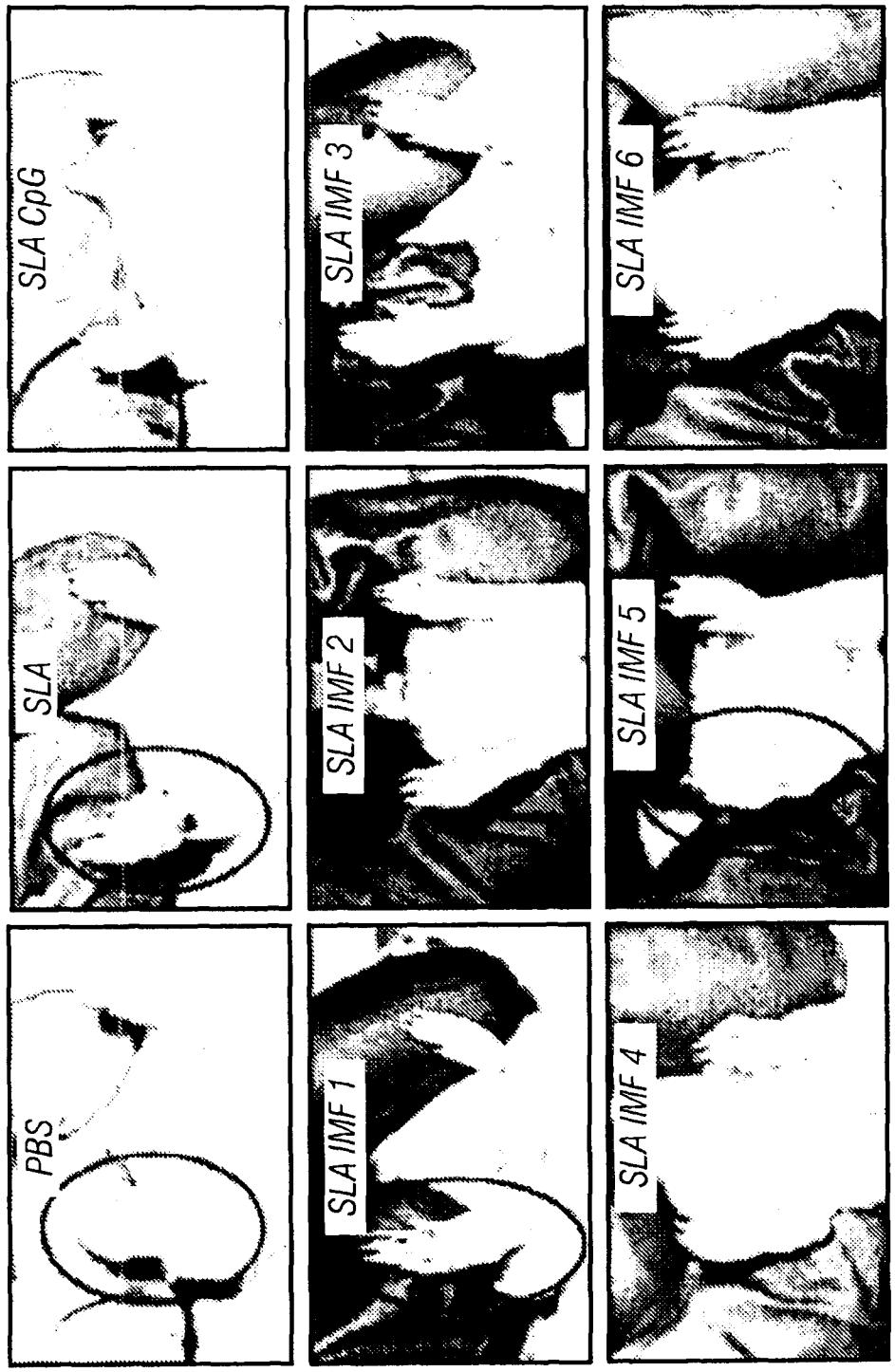
FIG. 8 shows the macroscopic state of injuries in the foot pads of animals vaccinated with SLA and SLA–CPG SLA.-IM versus control (PBS). In the figure are included photos of an animal in the control group, one vaccinated with SLA, one with SLA–CPG and the six vaccinated with SLA–IM, within the six weeks of infection.

Moreover, the macroscopic results 6 weeks post-infection are shown in FIG. 8, and demonstrate a significant reduction of the lesions in animals treated with SLA−CPG or SLA−IM in comparison with footpad form animals treated with SLA alone.

Figure 9:
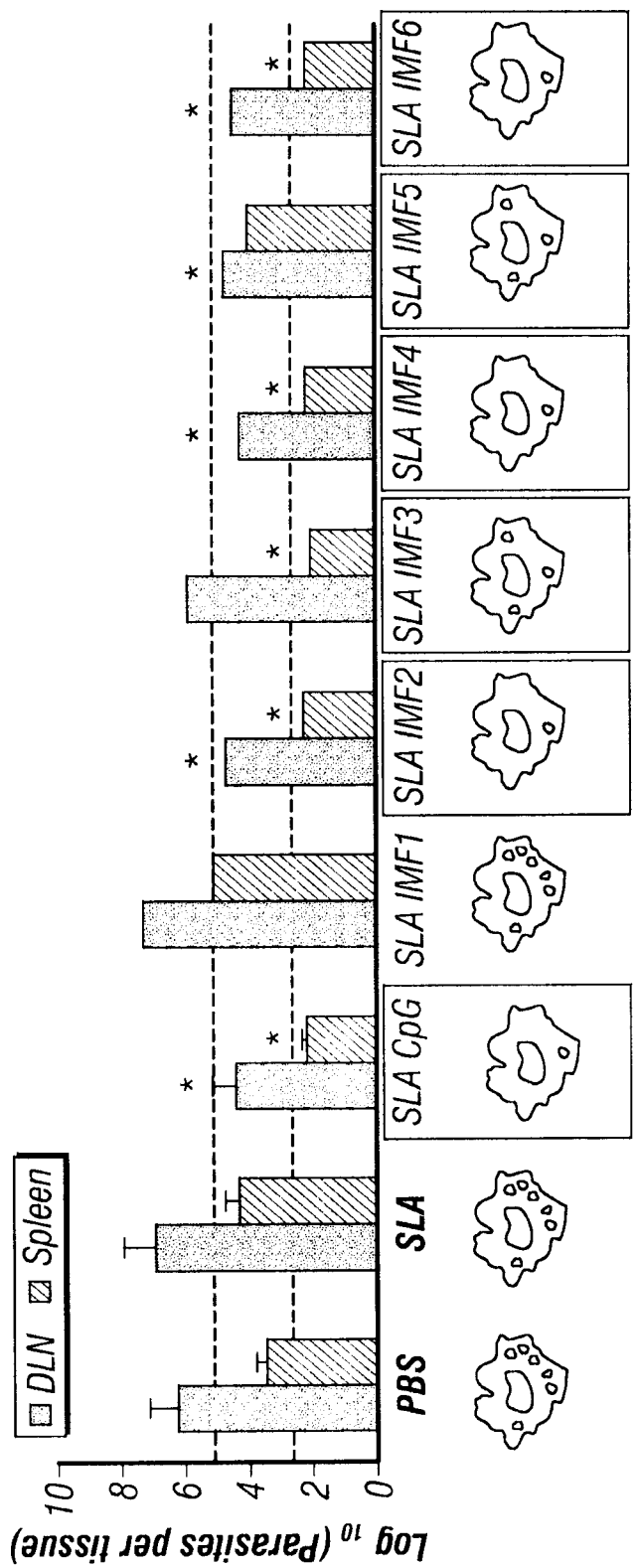
FIG. 9 shows the quantification of the number of parasites in the spleen and lymphoid nodes (DLN) wherein the immunization with SLA does not produce any reduction in the number of parasites counted in the cited organs with respect to the control group, while the SLA–CPG reduced a magnitude of approximately 2 logs that count and wherein the SLA–IM group obtained similar results for reduction.

Furthermore, the number of parasites was quantified in the footpad and spleen. At week 7 post-infection animals were sacrificed and parasites present at spleen and draining lymph nodes (DLN) determined. SLA immunization does not produce any reduction in the number of parasites in contrast to IM and CpG. CpG reduces this number in a magnitude close to 2 logs and IM showed similar results at least in 4 of the total of 6 animals (FIG. 9).

Briefly, SLA does not protect alone but its combination with CpG or IM has a protective effect against infection.

The spleen cells of the sacrificed animals were collected and stimulated "in vitro" with SLA and the Th1 (IFN-γ) and/or Th2 (IL-4) response evaluated.

Figure 10:
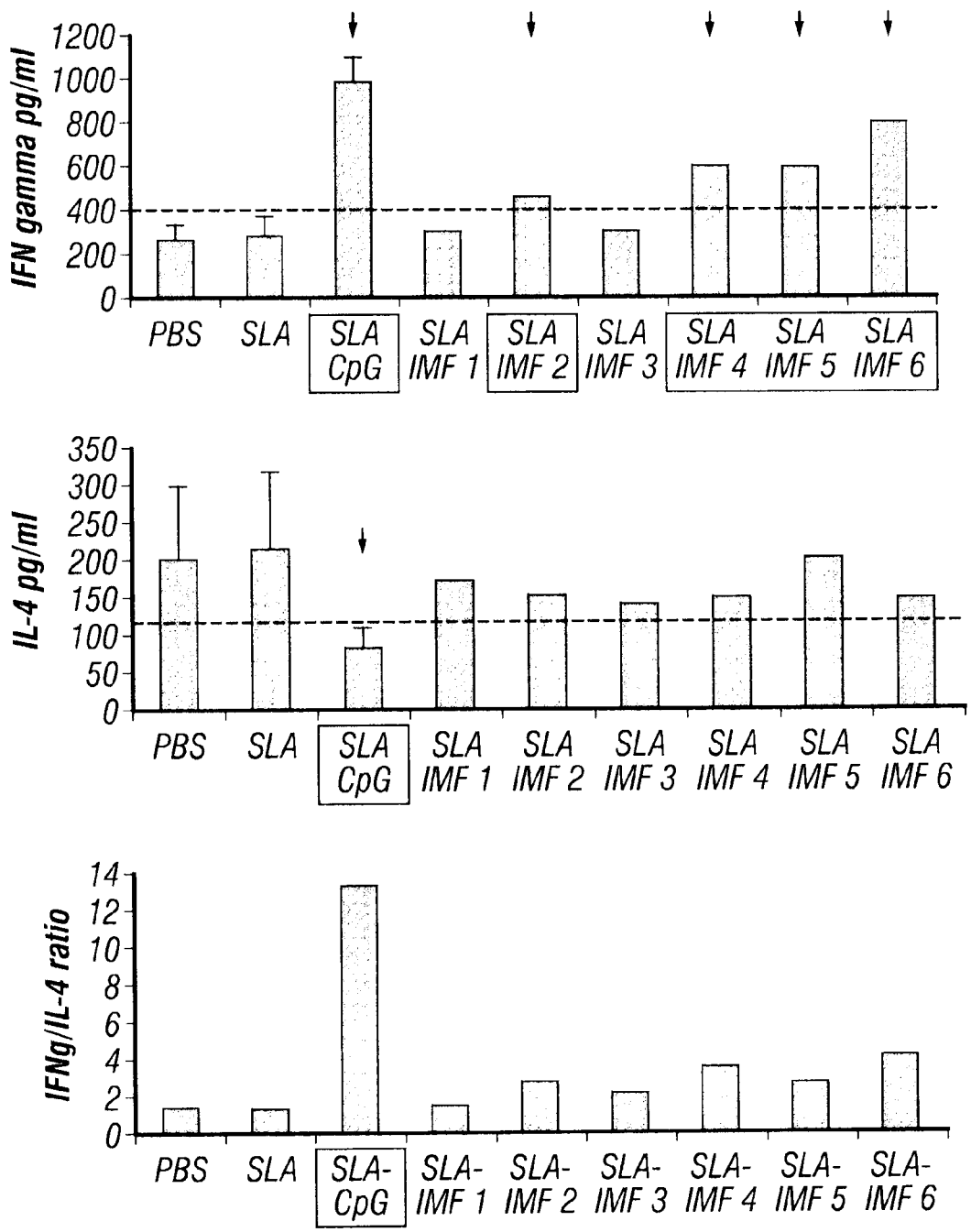
FIG. 10 shows the graphical results of the evaluation of the Th1 response (IFN-γ) and/or Th2 (IL-4) in cells from the spleens of sacrificed animals, while these isolated cells and stimulated in vitro with SLA.

*Leishmania major* infection in a susceptible Balb/c model enhance relatively the levels of IL-4 over those of IFN-γ is well described. Although SLA vaccination does not modify this pattern, its combination with CpG increases the Th1 response quantified by the production of IFN-γ and consequently lowered the relative expression of IL-4. Thus, the ratio IFN-γ (response Th1)/IL-4 (response Th2) increase significantly (FIG. 10).

Surprisingly, although IM has a similar and protective effect than CpG, the immunological pmecahanism is different. The protection does not strictly correlates with ratio of IFN-γ (response Th1)/IL-4 (response Th2), since both parameters increases at same time (FIG. 10).

A second way to determine the response Th1/Th2 is to analyse the levels of the *Leishmania*-specific isotype antibodies IgG2a (Th1) and IgG1 (Th2).

Figure 11:
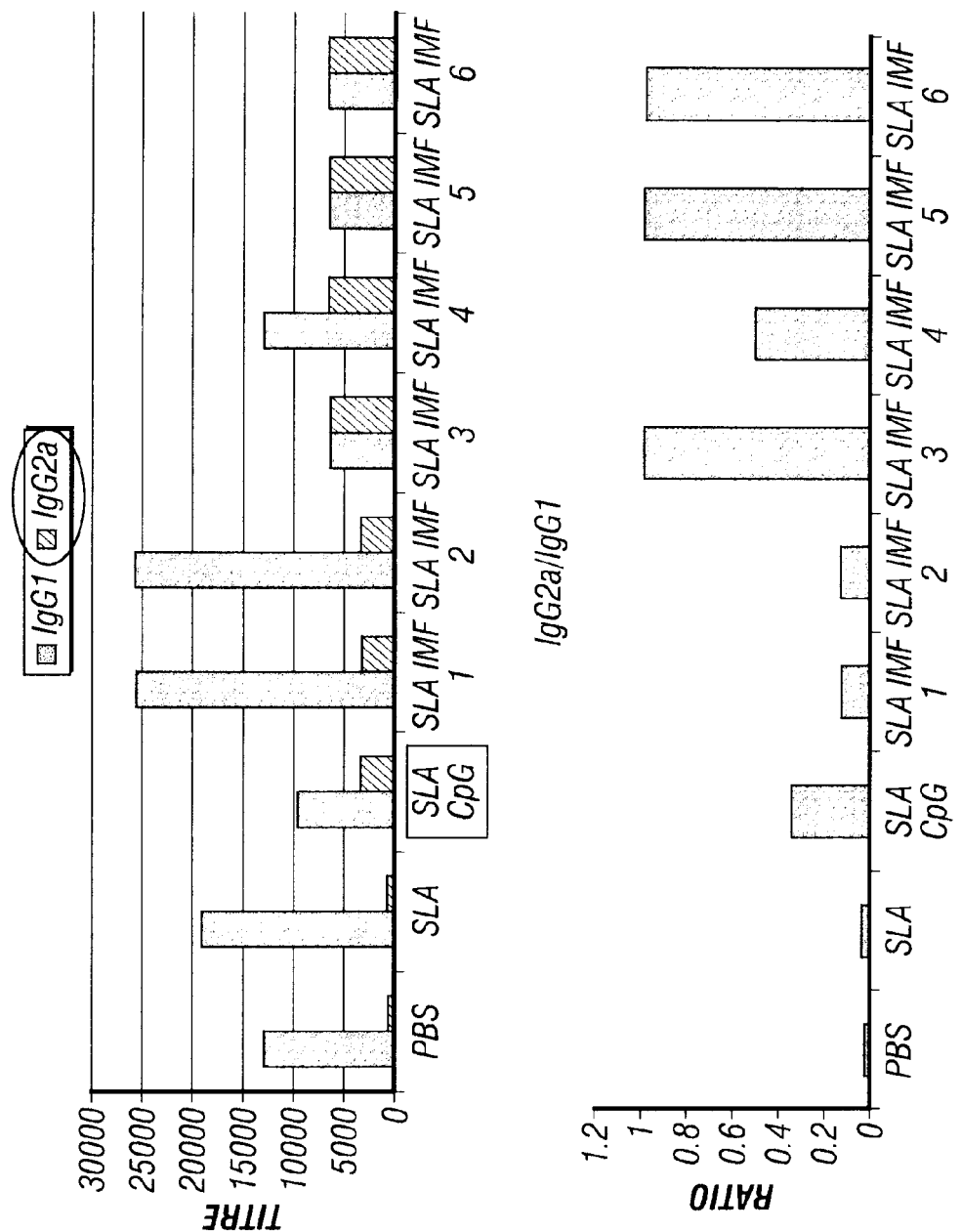
FIG. 11 shows the evaluation of the Th1/Th2 response depending on the analysis of levels of *Leishmania* in respect of specific antibody isotypes IgG2a (Th1) and IgG1 (Th2).

Although it is not clear the mechanism, the levels of IgG2a is correlated with protection against *Leishmania*. In animals not treated or treated only with SLA no levels of IgG2a were detected. However, levels of IgG2a were detect in animals treated with CpG or IM. Thus, the ratio IgG2a/IgG1 is low in animals non-treated or treated only with SLA in contrast with those in the SLA−CPG and SLA−IM groups (FIG. 11).

Figure 12:
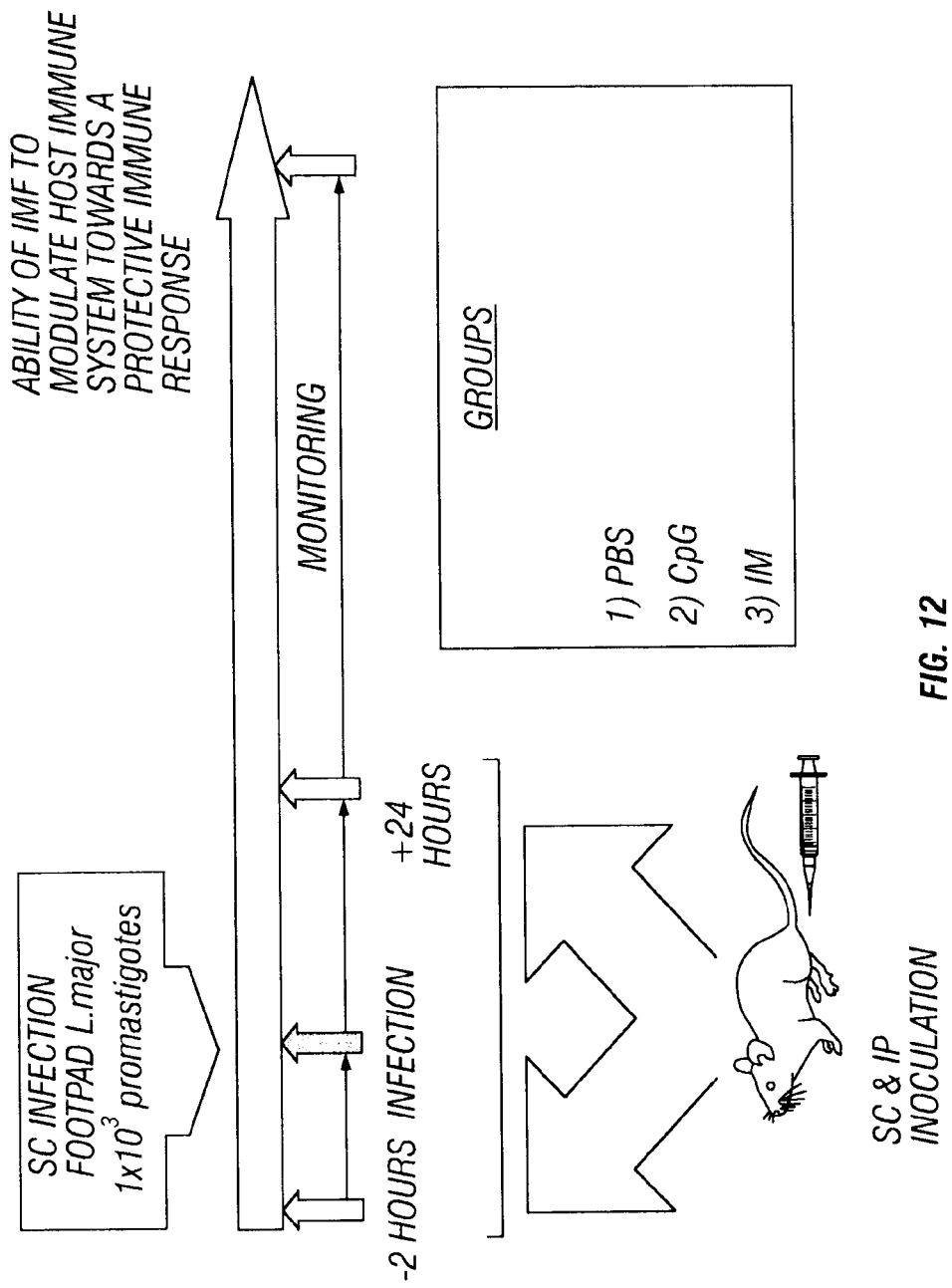
FIG. 12 shows the protocol for evaluating the therapeutic effect of IM in an experimental infection with *Leishmania*.

Protective And Therapeutic Effect of the IM In the Footpad Experimental Mouse Model:

In the FIG. 12 it is shown the protocol to evaluate the therapeuctic effect of IM in an ongoing experimental infection with *Leishmania*.

For this, IM were inoculated at same time than *Leishmania* with two different doses:

1) Group IMF-1, 2 and 3, receiving 0.6 µg/Kg (18 ng/mouse)
2) Group IMF-4, 5 and 6, receiving a dose of 1.2 µg/Kg (36 ng/mouse).

Figure 13A:
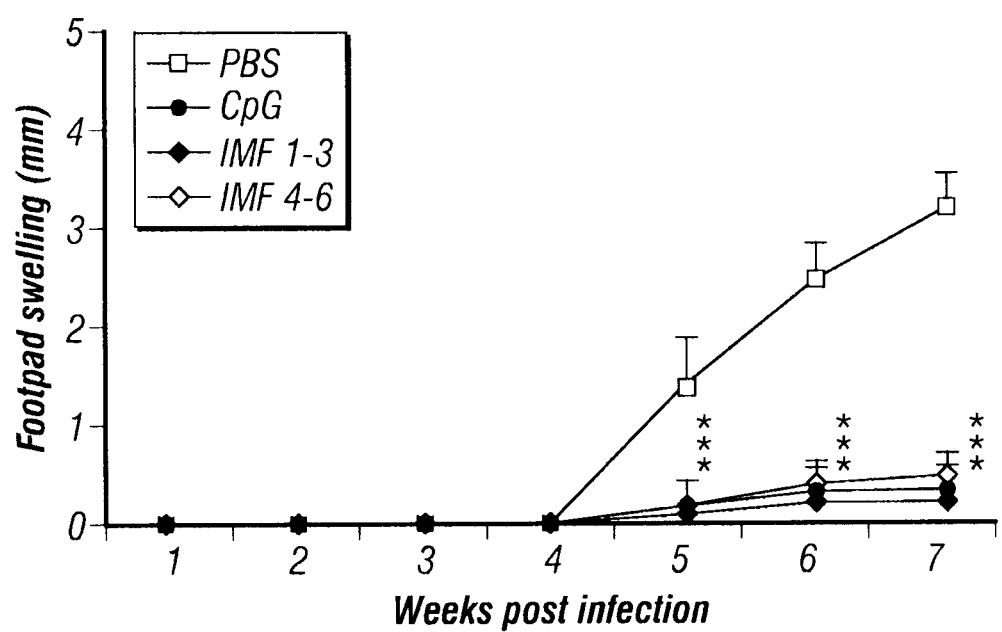

The results show that IM is able to protect with similar potency than those obtained with CpG against infection with *Leishmania major* (FIG. 13 A).

Figure 13B:

The animals treated with IM did not show any remarkable lesions (FIG. 13B). After 7 weeks of the infection animals were slaughtered and quantified the number of parasites in spleen and lymph nodes (LN). Similar results were obtained in the Groups CpG and IM with a significant reduction (10.000 times) in lymph nodes and not parasites were found in Spleen (FIG. 13C).

Finally and in concordance with the previous experiments, CpG group induces a significant change in the ratio of the levels of the antibodies IgG2a/IgG1. Moreover, IM does not show significant change in this ratio also in agreement with the previous results obtained (FIG. 14).

As a final conclusion, we found that IM has similar properties than CpG but differs from the last in the immune mechanism, due to not change the profile and ratio of the Th1/Th2 or the IgG2a/IgG1. In this context, IM could be better adjuvant due to the activation of both responses (not only Th1 as demonstrated in CpG).

IM (LPS of *Ochrobactrum Intermedium*) Has Vaccine Adjuvant Properties In Immunosuppresed Animals:

IM has been shown previously to have a vaccine adjuvant effect on *Leishmania* infection using SLA as the antigen.

This antigen is poorly immunogenic and more importantly mostly induces a Th2 response (characterized by a predominance of IgG1 antibodies and IL-4 production), and not a Th1 response (characterized by an IgG2a response and IFN-gamma production) which is the protective one.

Figure 15:
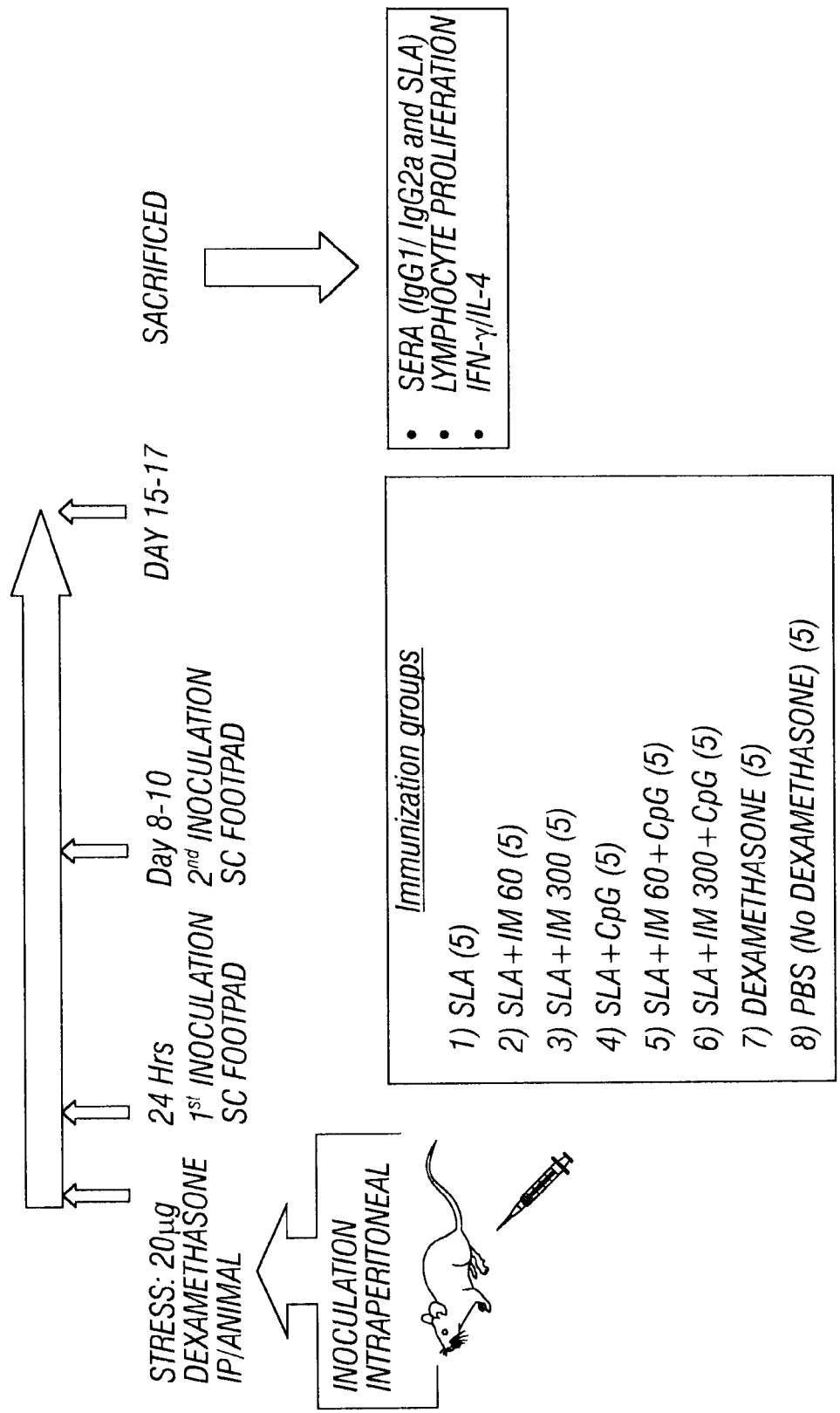
FIG. 15 shows the outline of the protocol used to analyze the role of adjuvant RT in immunosuppressed animals. Groups of 5 animals were immunosuppressed with dexamethasone and vaccinated with SLA, SLA–CPG or SLA–IM. After 24 hours, the animals were infected and later reinfected at day 8. After sacrifice at day 60, it is evaluated the evolution of the lesion and the immune parameters.

To test the adjuvant effect on immunosuppressed mice, Balb/c females were treated with the corticosteroid Dexamethasone (Dex), 20 µg IP/animal, and 24 hr later the animals were inoculated with SLA alone (10 µg/animal) or in combination with IM, 0.6 µg/Kg (dose 60) or 3 µg/Kg (dose 300), or CpG, a compound previously reported to induce Th1 responses (see FIG. 15 for the protocol used). Mice were boosted a week later with SLA alone and at 17 days, the animals were sacrificed and spleen cells were collected and anti-SLA titters in the serum evaluated.

Figure 16:
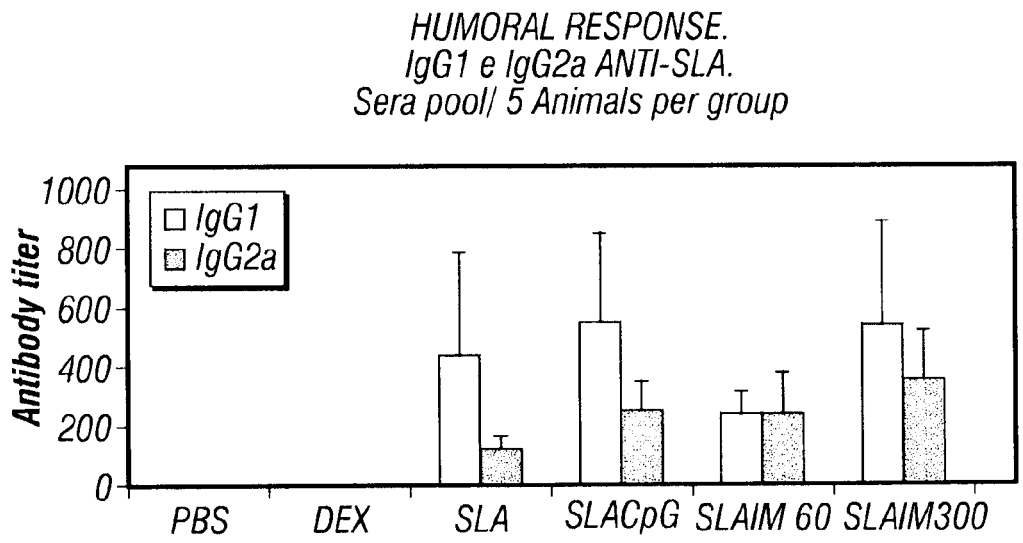
FIG. 16 shows the adjuvant effect of IM after vaccination with SLA in spleen cells of mice. The spleen cells were cultured with or without antigen SLA (10 g/ml) for 72 hours and proliferation assessed by incorporation of trimidina to the DNA over a period of 72 hours. The results show the average of 2 experiments in triplicate using 6 animals in each experiment.

As shown in FIG. 16, specific ant-SLA antibodies were detected in all animals injected with SLA but not in controls with Dex alone, but most of the antibodies were of the IgG1 isotype. As reported, CpG adjuvant increased IgG2a/IgG1 ratio and more importantly IM was better than CPG in inducing this shift, representative of a Th2 to Th1 switch in vivo. This indicated that IM has adjuvant activity in immunosupressed animals, and more importantly if keeps favouring Th1 responses even in immunosupresed animals.

Figure 17:
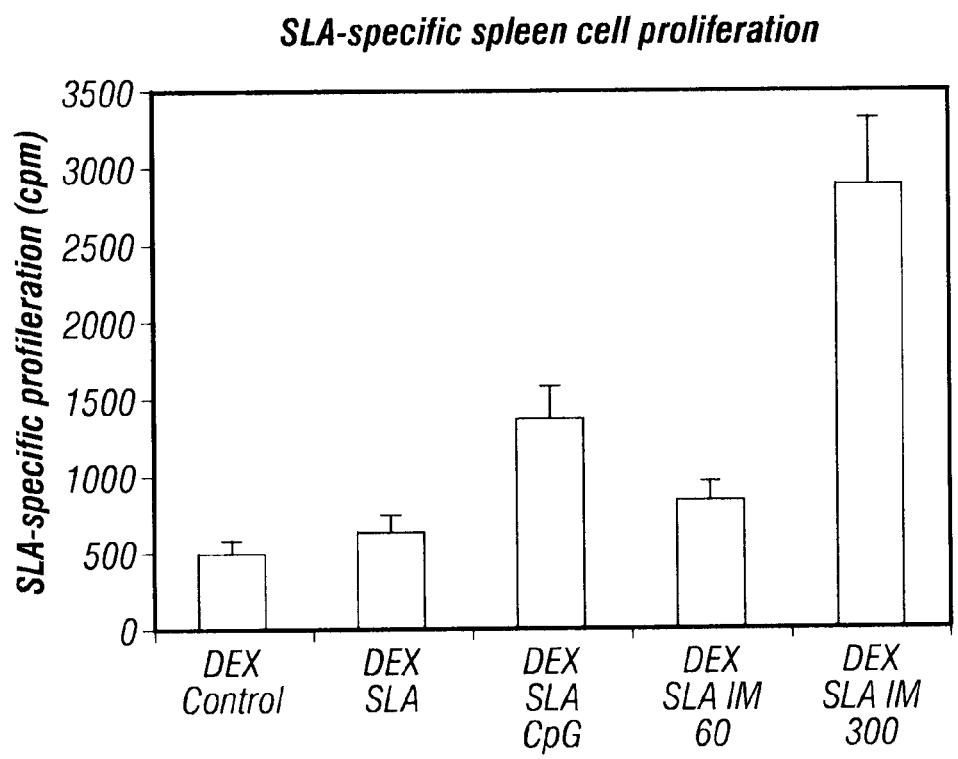
FIG. 17 shows the effect on IL-4 production by spleen cells from vaccinated animals. The spleen cells were isolated from various animals and stimulated SLA (10 g/ml) and analyzed by ELISA the secretion of IL-4.

In addition, spleen cells from the different animals were obtained and stimulated in vitro with SLA and proliferation and IFN-γ (a Th1 cytokine required for protection against *Leishmania*) were measured. As shown in FIG. 7, SLA induced a proliferative response in Dex-treated animals. CpG treated animals have an improved proliferative response. Interestingly, animals treated with IM have also better proliferative response to SLA in a dose response manner (FIG. 17). No differences in response to mitogens were observed among all animals (not shown).

Figure 18:
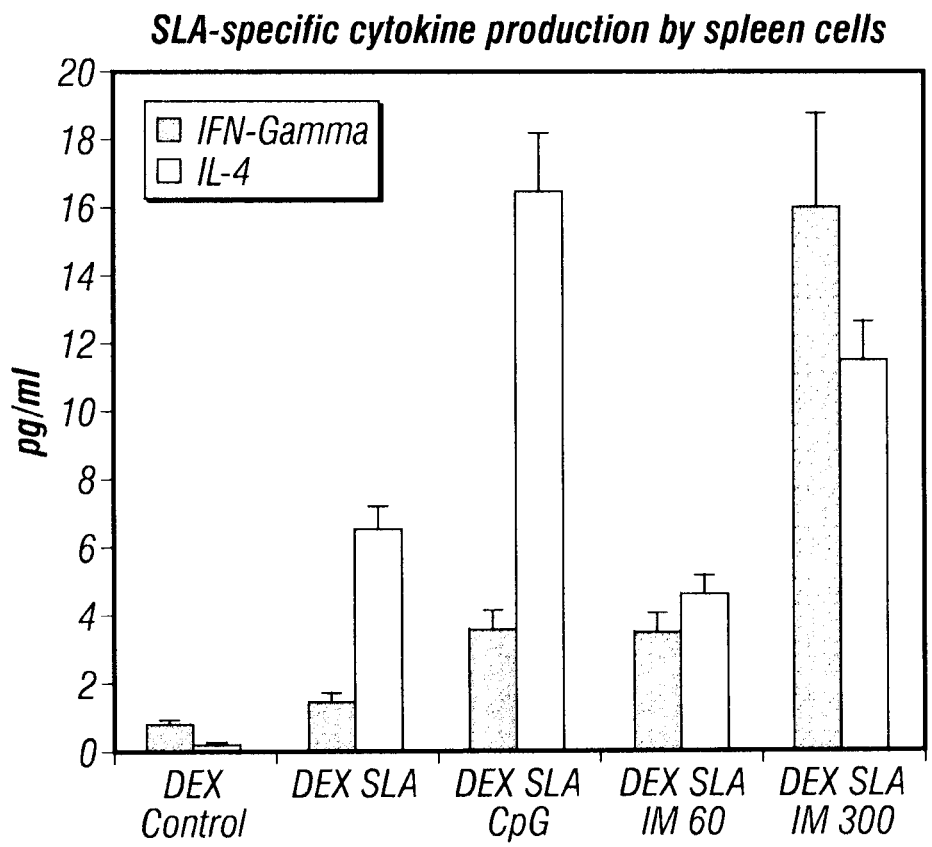
FIG. 18 shows the effect of IL-4 and IFN-gamma by spleen cells of mice vaccinated and treated with dexamethasone (DEX).

We checked IFN-γ (a Th1 cytokine) and IL-4 (a Th2 cytokine) released in the supernatants of spleen cells after SLA treatment of spleen cells "in vitro". As shown in FIG. 18, Dex control animals not vaccinated have no detectable production of IL-4 or IFN-γ upon SLA challenge in vitro. In SLA-vaccinated animals, SLA "in vitro" challenge, results in IL-4 production but very little IFN-γ in agreement with IgG1/IgG2a data on the serum of the same animals.

Figure 19:
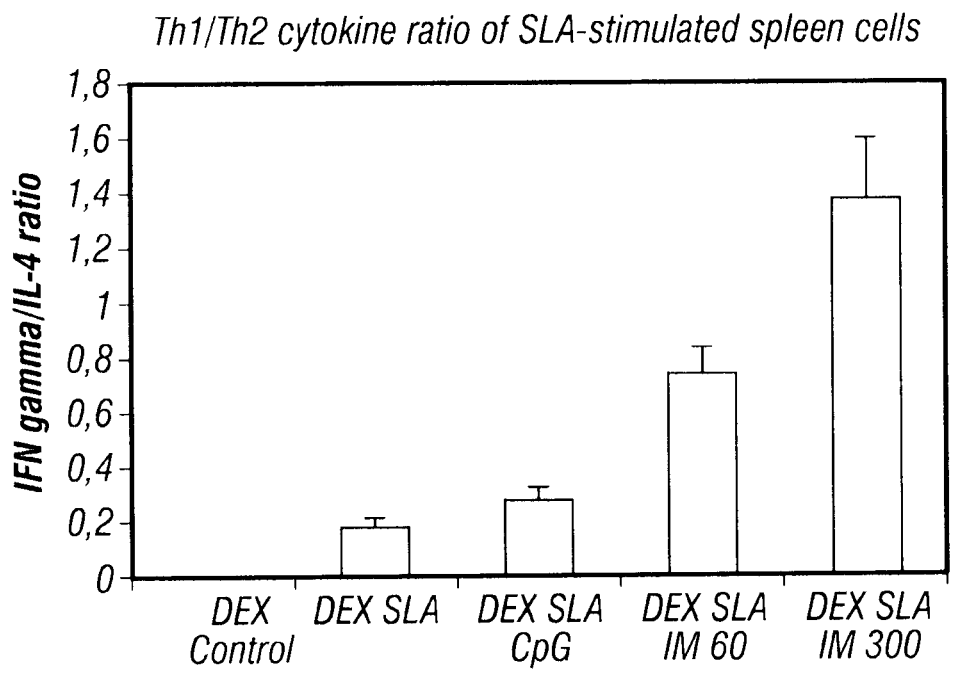
FIG. 19 shows the cell response to SLA in vaccinated animals. It shows the specific response against IFN-gamma and response to SLA 17 days after the addition in vitro of the SLA. It shows the ratio of IFN-gamma secretion (Th1)/IL-4 (Th2).
Figure 20:
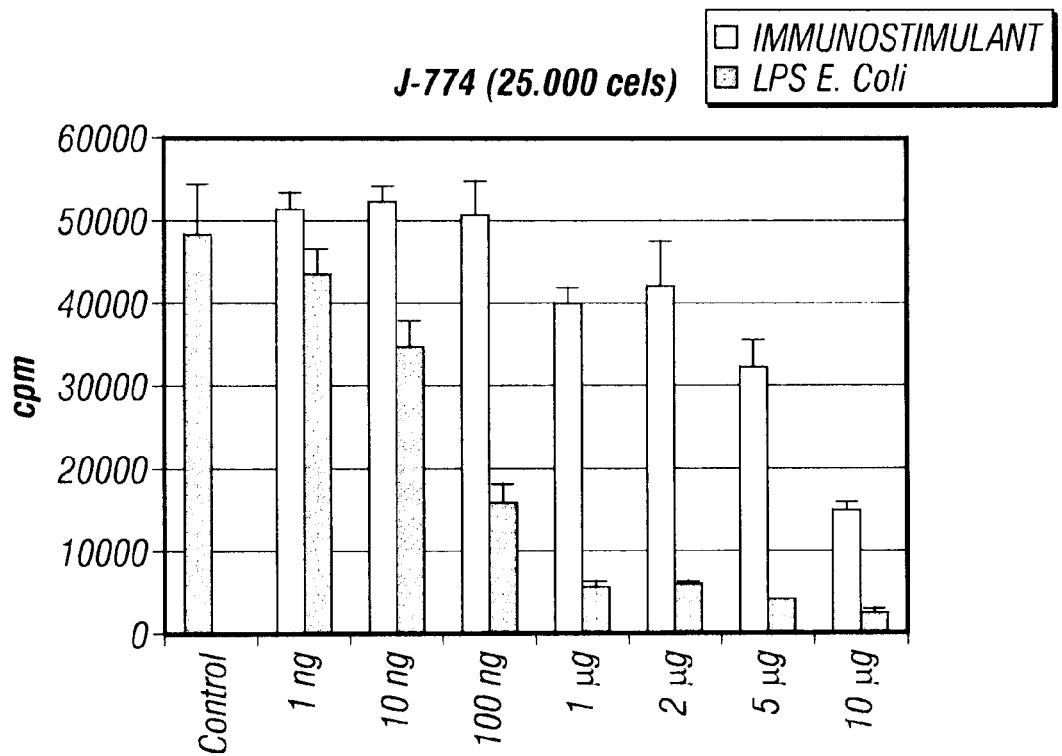
FIG. 20 shows the differentiation of J774 cells after addition Immunostimulant compound compared with $E.$ $coli$ LPS in Raw macrophages. The Immunostimulant compound of the invention induces a dose-dependent inhibition of the differentiation of J774 macrophages. This effect is around 500 less potent than the one observed with LPS from $E.$ $coli$ on weight/vol basis in J774 or Raw macrophages (not showed).
Figure 21A:
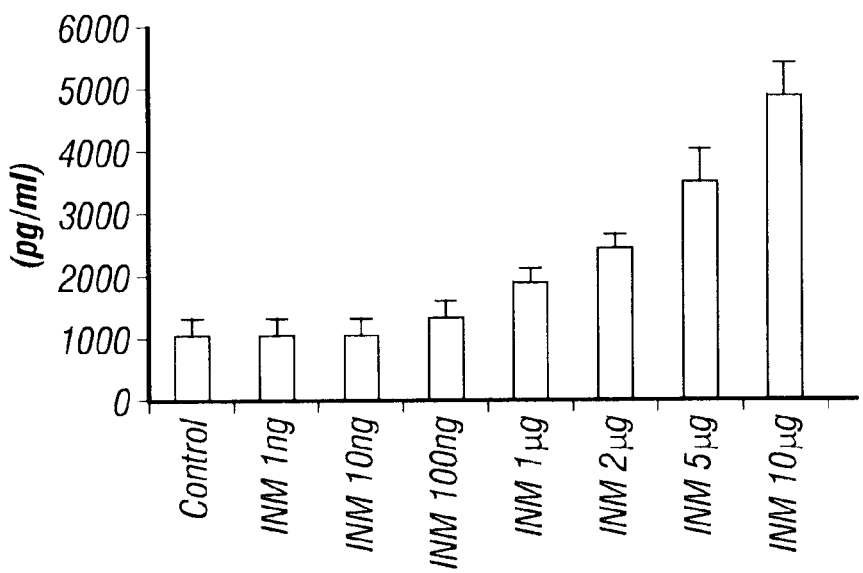
FIGS. 21A and B show that unstimulated macrophages do not synthesize TNF detectable by ELISA. The immunostimulant composition of the invention at doses 0.1-10 µg/ml induces in a dose response manner significant TNF production reactivity levels up to 4000 pg/ml in J774 macrophages (FIG. 21A) as well in raw cells (not showed). The effect of the immunostimulant of the invention although highly significant was around 500 fold less potent than LPS from $E.$ $coli$ (FIG. 21B)
Figure 21B:
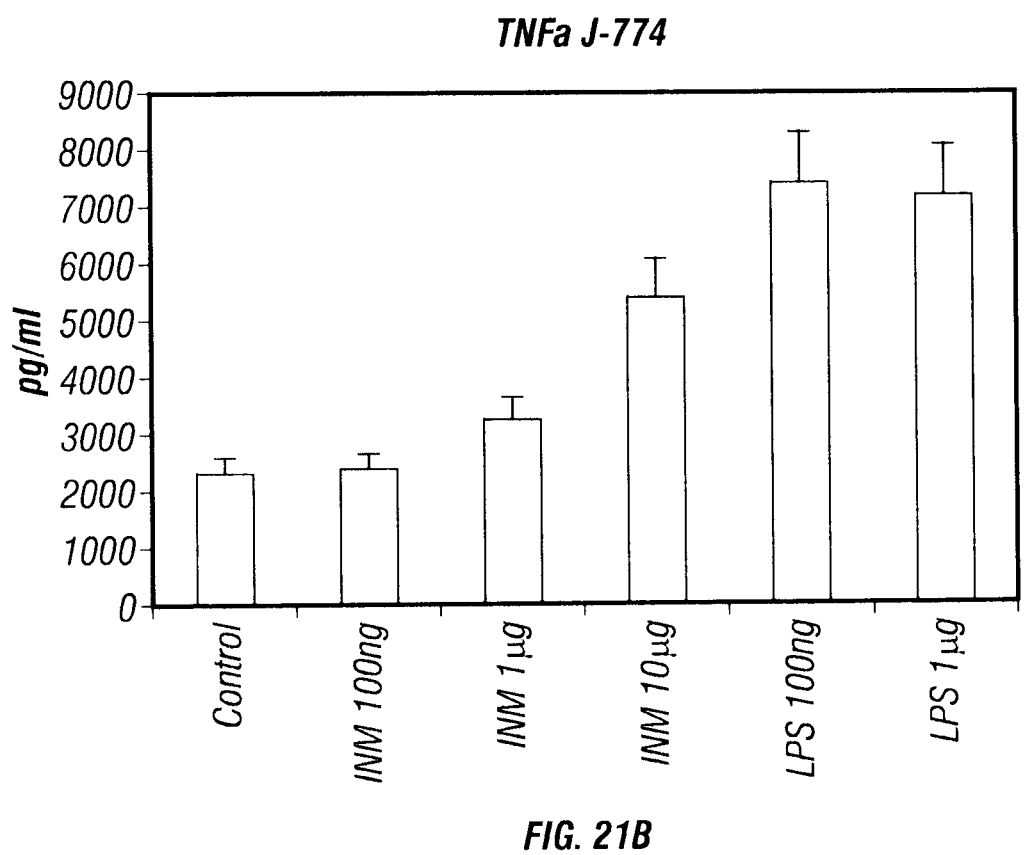
Figure 22:
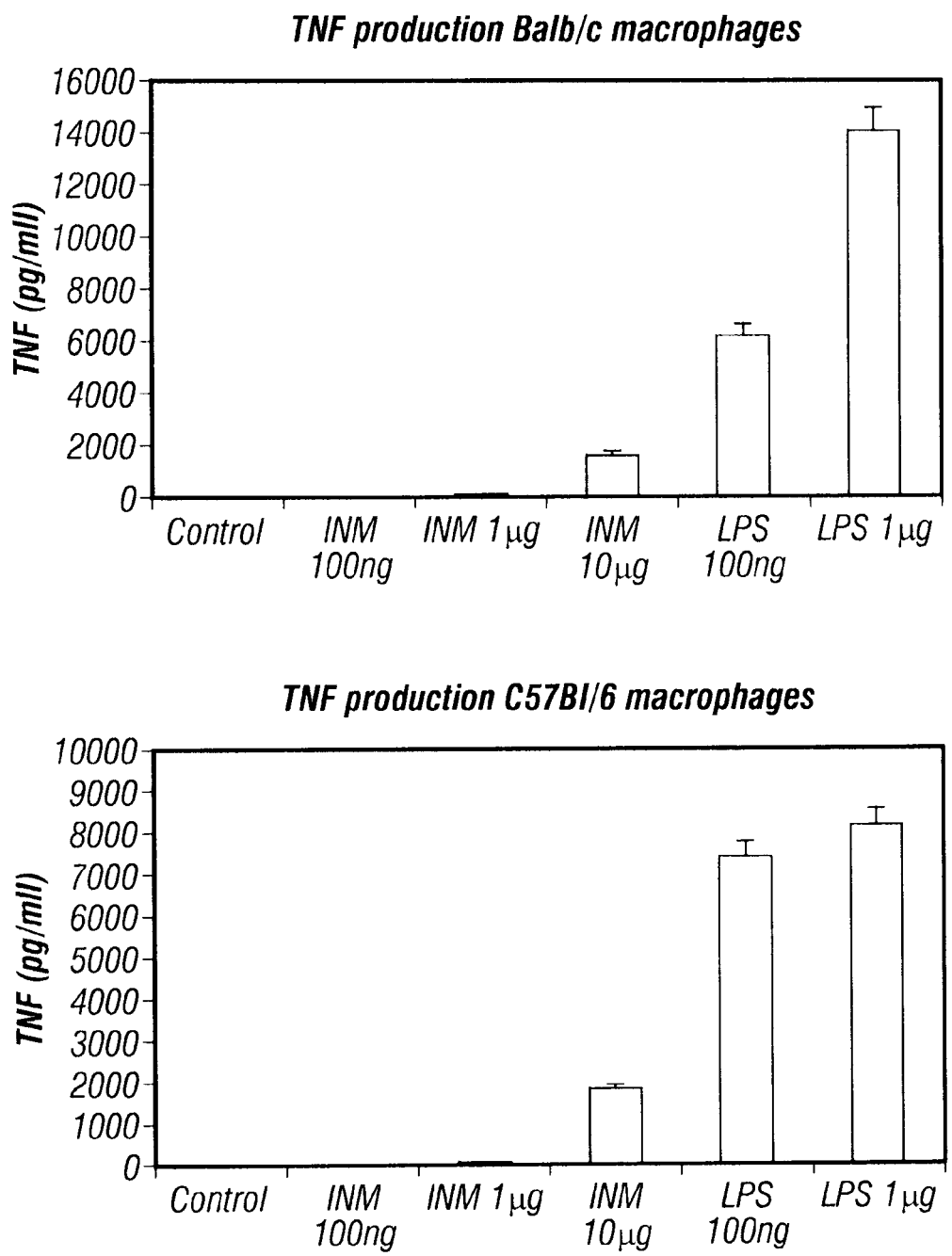
FIG. 22 shows the immunostimulant composition of the invention induces TNF production in macrophages from both Balb/c and C57B16 strains of mice, although with less potency than $E.$ $coli$ LPS at equivalent concentrations (FIG. 3).
Figure 23:
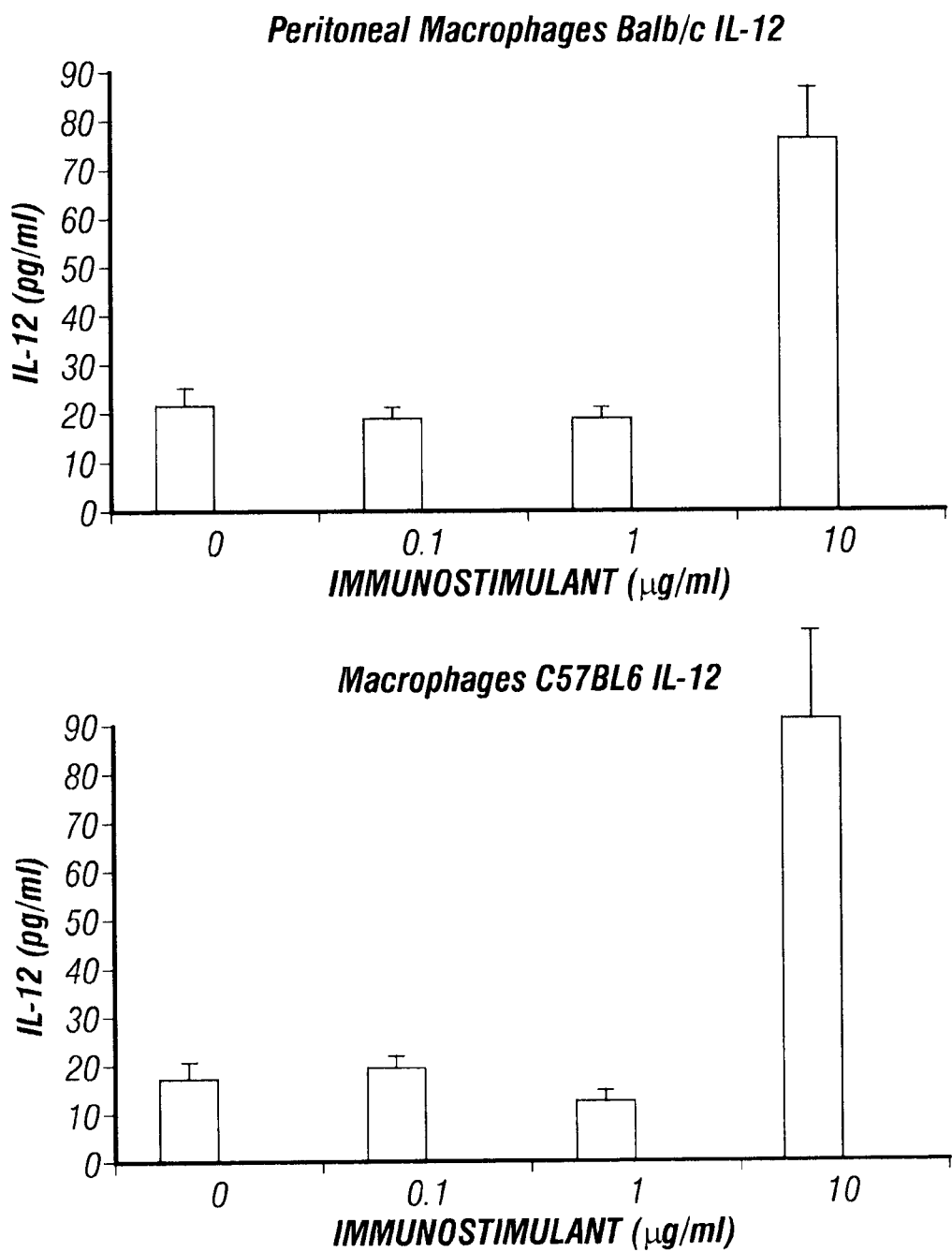
FIG. 23 shows the immunostimulant of the invention at doses of 10 m µg/ml induces large amounts of IL-12 in peritoneal macrophages from both C57BI/6 and Balb/c (FIG. 4)
Figure 24:
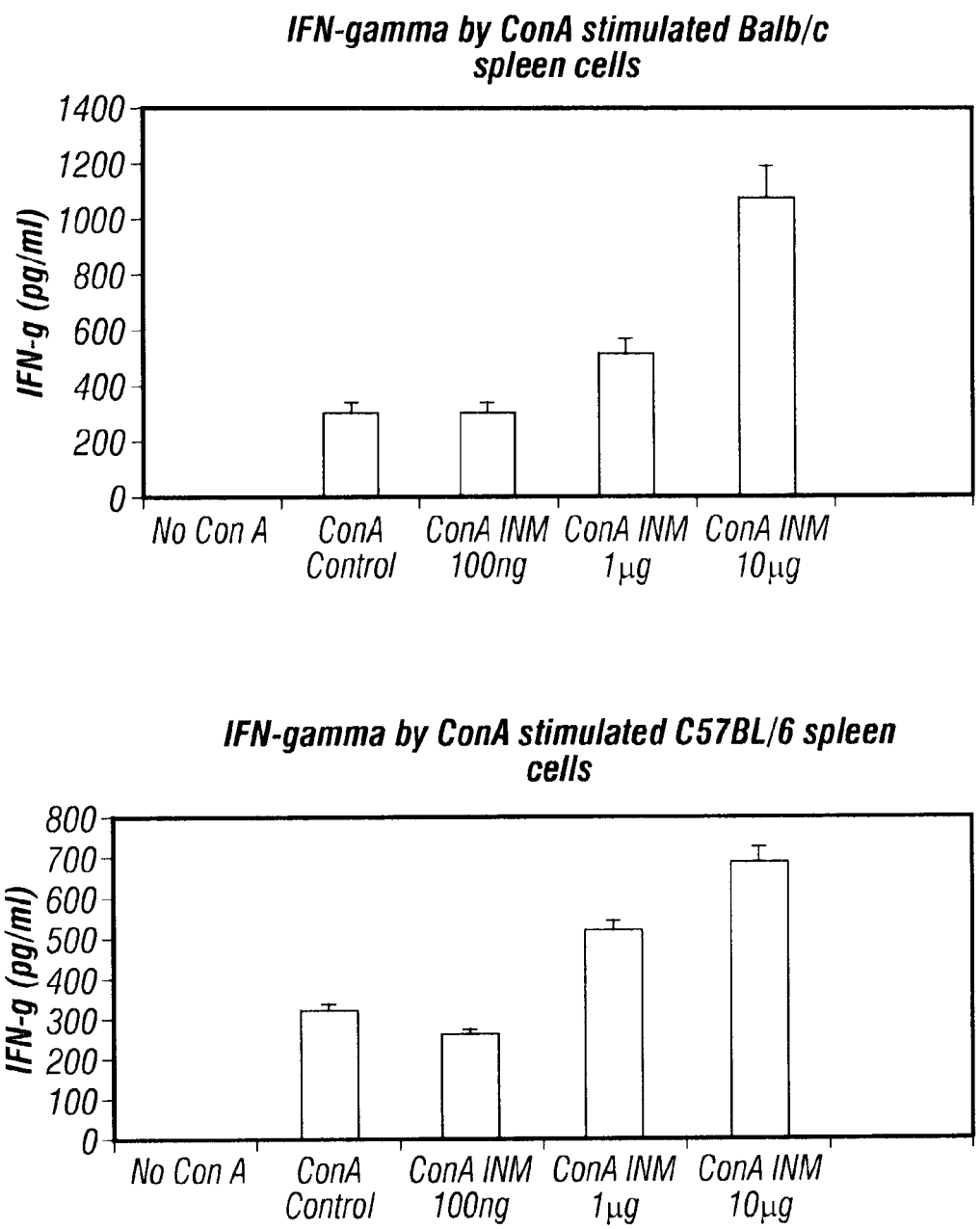
FIG. 24 shows the stimulation induces a large amount of IFN-gamma secretion by spleen cells from both strains of mice, suggestive of stimulating a Th1 response characterized by the production of IFN gamma. The Immunostimulant composition of the invention at doses of 1-10 mµg/ml induces large amounts of IFN gamma spleen lymphocytes from both C57BI/6 and Balb/c.
Figure 25:
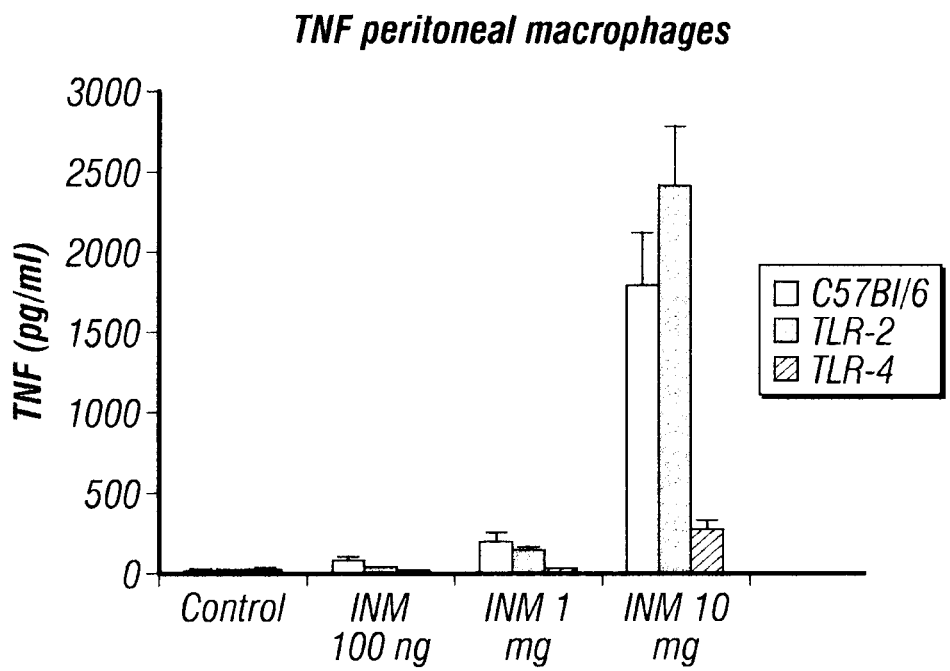
FIG. 25 shows the immunostimulant composition of the invention induce TNF in peritoneal macrophages from C57BI/6 whereas TLR-2 deficiency only partially prevents the activity and lack of TLR4 in macrophages strongly decreased the induction.
Figure 26:
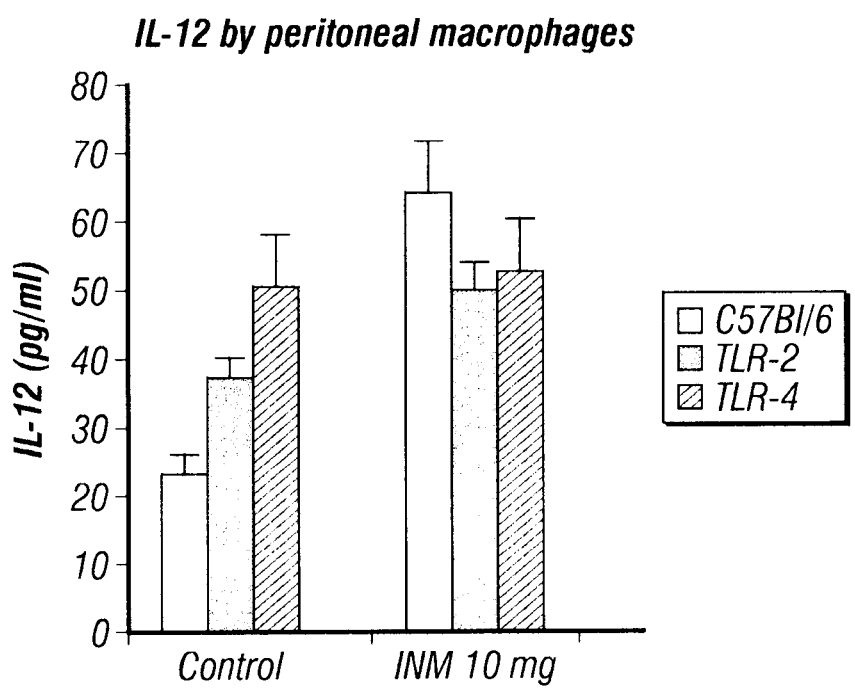
FIG. 26 shows the immunostimulant composition of the invention induces IL-12 in peritoneal macrophages from C57BI/6 whereas TLR-2 deficiency only partially prevents the activity and lack of TLR4 in macrophages strongly decreased the induction.
Figure 27:
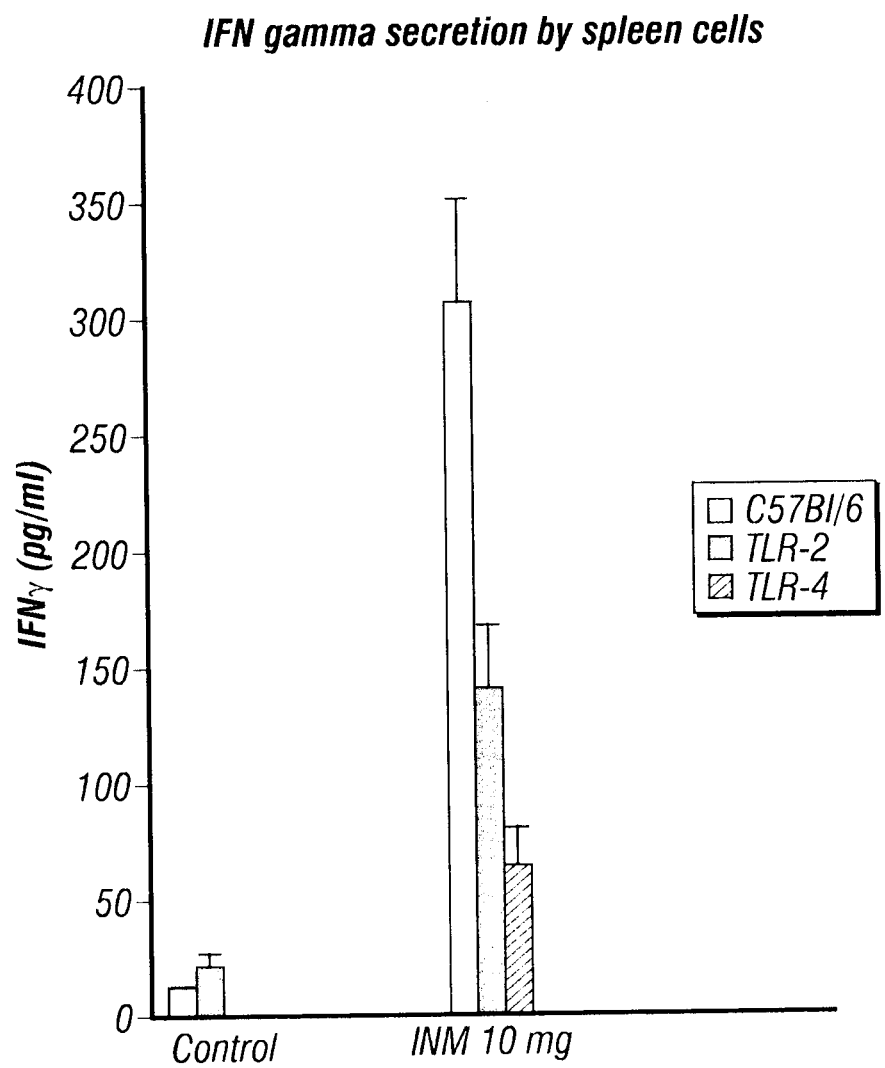
FIG. 27 shows stimulation induces IFN-gamma secretion, that was severely depressed in spleen cells from C57BI/6 tlr2−/− and almost completely disappeared when C57BI/6 tlr4−/− cell were used 10 mg of immunostimulant compound.
Figure 28A:
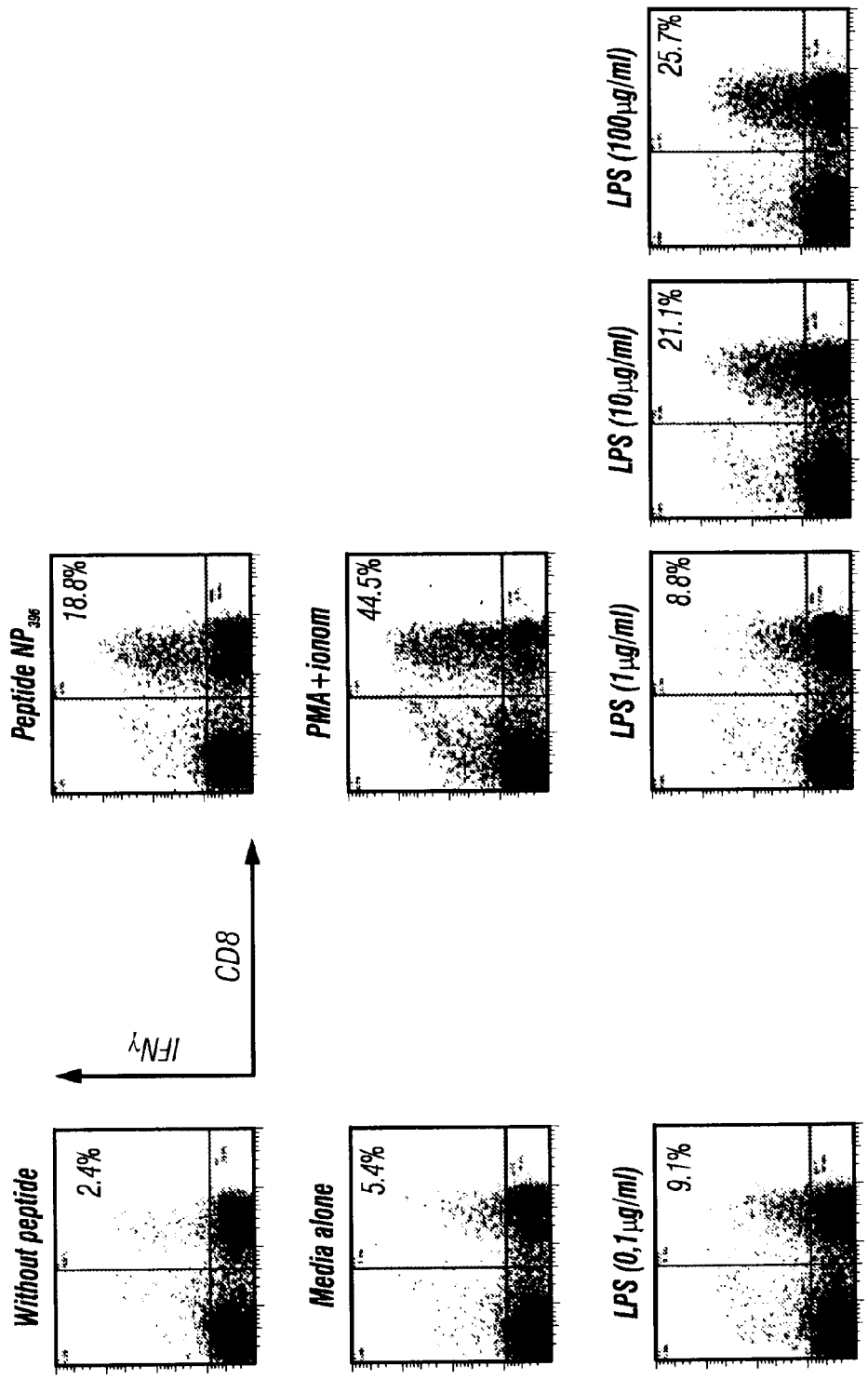
FIGS. 28A and B show cell response CD4(FIG. 28A) or CD8 (FIG. 28B) induced after infection with Lymphochoremeningitis virus in spleen cells from B6 C57 mice and addition of different stimuli; from the left to the right: non peptide; LCMV NP 396 peptide (PEPTIDE NP 396); media alone; PMA plus ionomycing; and immunostimulant compound at different concentrations.
Figure 28B:
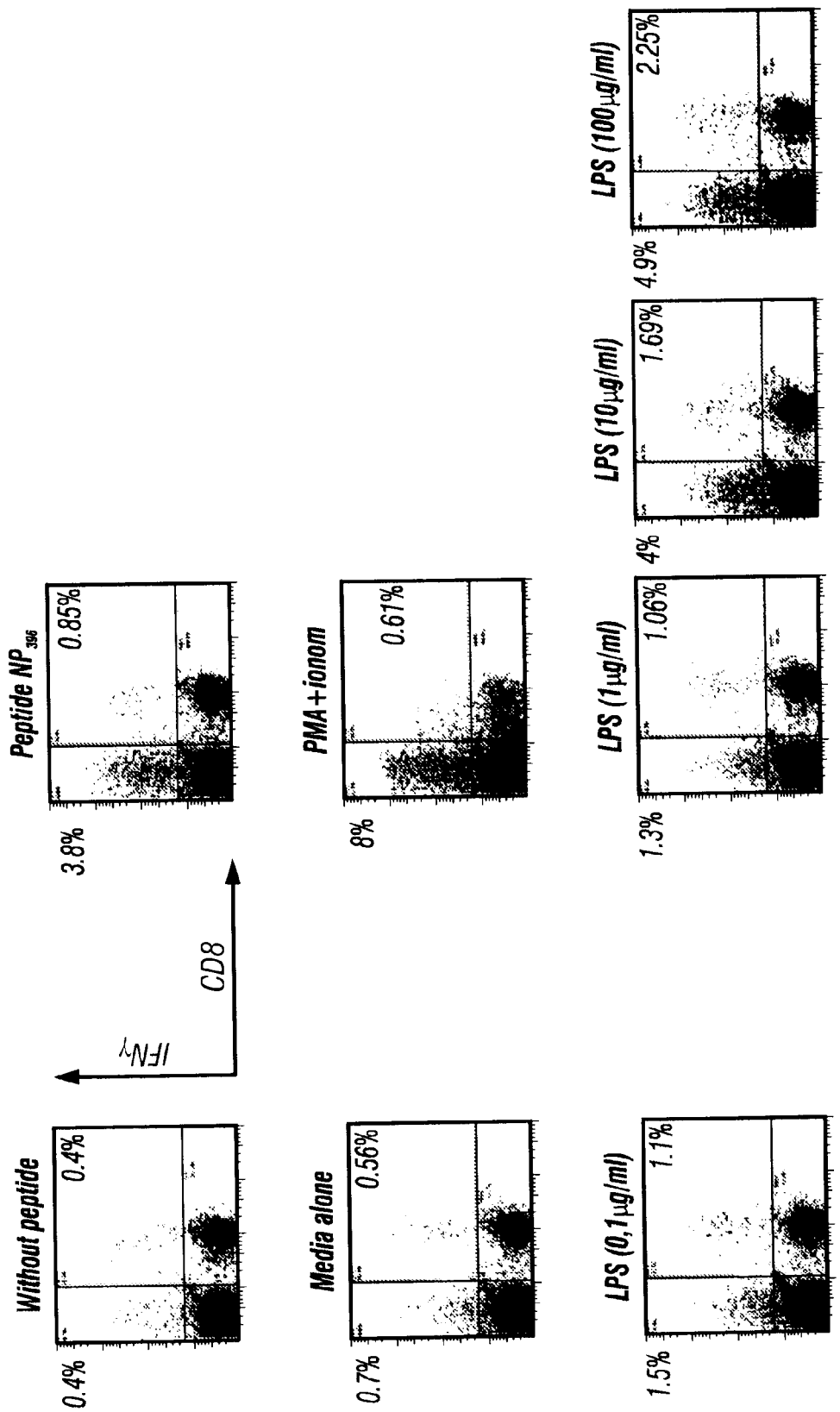
Figure 29A:
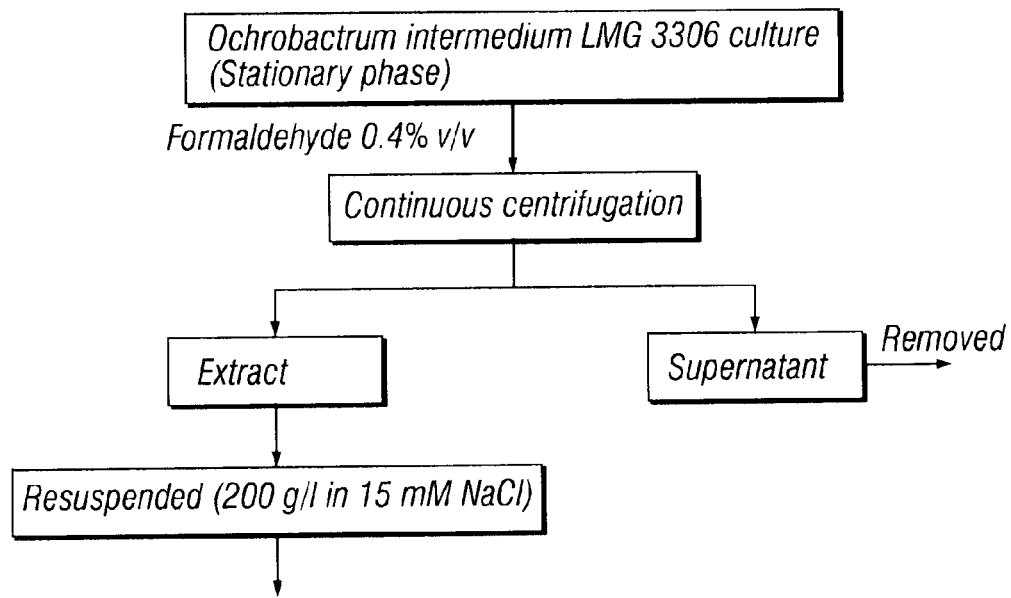
FIGS. 29A and B show the flow chart of an extraction method of $Ochrobactrum$ $intermedium$ LMC; 3306 LP.
Figure 29B:
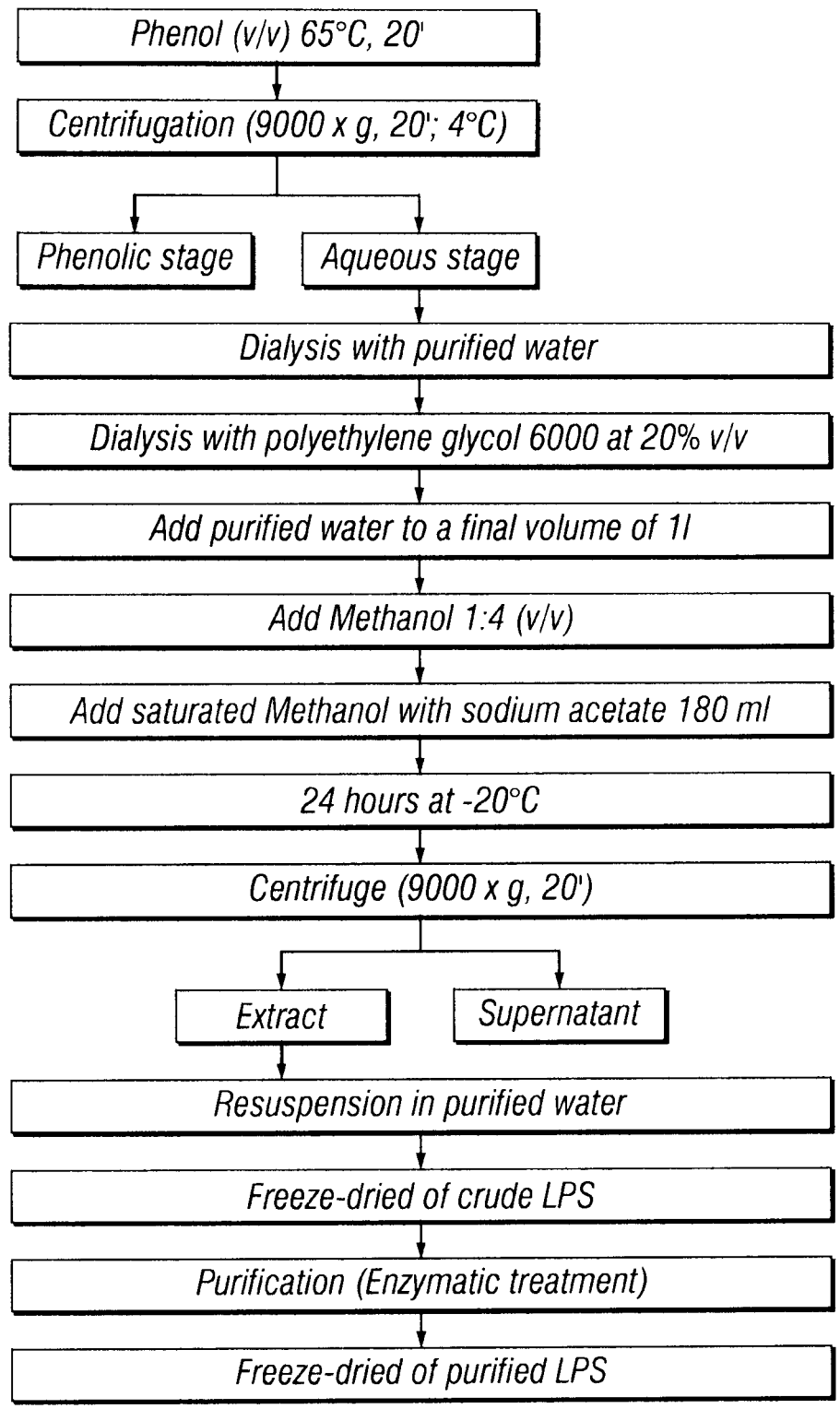
Figure 30:
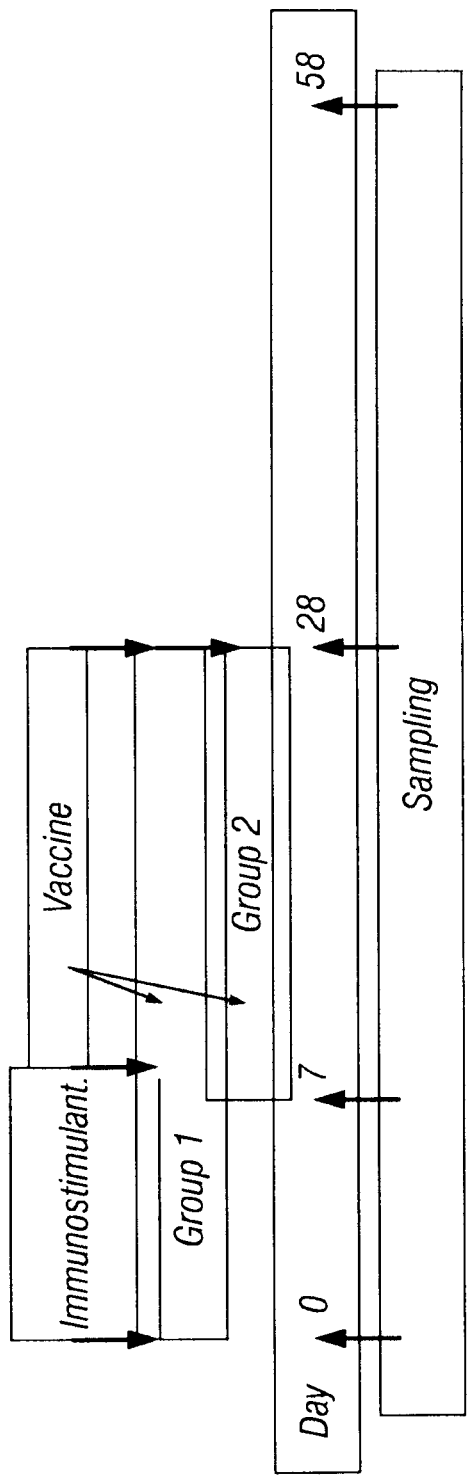
FIG. 30 shows the test development scheme.

CpG treatment induced both an increase in IL-4 and in IFN-γ without altering much their ratio (FIG. 19). Interestingly, LPS of IM increased also both cytokines but in much higher proportion IFN-γ than IL-4. This was especially evident in animals treated with 3 μg/Kg (dose 300), a 10 fold increase in IFN-γ/IL-4 ratio (FIG. 19).

EXAMPLE 2

Manufacturing Method

The immunostimulant LPS was obtained from *O. intermedium* strain LMG 3306 following the manufacturing process described above.

1. Method to obtain the fermentation bulk antigen as according to part (ii) described above (Manufacturing process)
2. Method of extraction LPS as according to part (iii) described above (Manufacturing process)
3. Purification and calculation of LPS amount as according to parts (iv) and (v) described above (Manufacturing process)

The product was stored in a stainless steel tank that has been previously sterilized and provided with a continuous stirring system, in order to keep the homogeneity of the batch for up to 24 hours at 4° C. The product was transferred from the tank to the bottling area using sterile gas tube system.

Bottling was carried out in a sterile environment, class 100 A, with 100 B background. Rubber stoppers and capsules were applied in the same area.

The vials containing the final product were stored at 4° C., until they were labeled and packed. Labeling and packing were carried out in a separated area, and only one batch of the final product and its conditioning material can enter this area each time. Final storage until marketing was carried out at 5±3° C.

EXAMPLE 3

Composition

| NAME OF SUBSTANCES | QUANTITY PER DOSE (1 ml) |
|---|---|
| Active substances: | |
| LPS *Ochrobactrum intermedium* LMG3306 | 6 μg |
| Excipients: | |
| Water for injection | 1 ml |

EXAMPLE 4

Kdo Test

The main objective of this study is to check the repetitivity of the determination of the nanomols per ml of LPS following the colorimetric method of Kdo described above.

The parameters to be examined were:
1-Intra-assay precision
2-Inter-assay precision
3-Inter-batch precision
1-Intra-Assay Precision Results In this assay, one batch of the product of the invention (A003A) was used, 3 samples were titrated the same day with 10 replicates per sample. Then, three dilutions (½, ¼ and ⅛) of each sample, with 10 replicates per dilution were tested to check the repetitivity of the assay.

Results:

| Sample | 1 | 2 | 3 | 4 | 5 | 6 | 7 | 8 | 9 | 10 |
|---|---|---|---|---|---|---|---|---|---|---|
| 1 | 0.25 | 0.25 | 0.25 | 0.26 | 0.25 | 0.25 | 0.24 | 0.25 | 0.25 | 0.25 |
| 2 | 0.25 | 0.25 | 0.25 | 0.25 | 0.25 | 0.25 | 0.25 | 0.25 | 0.25 | 0.25 |
| 3 | 0.25 | 0.26 | 0.25 | 0.25 | 0.25 | 0.25 | 0.25 | 0.25 | 0.25 | 0.25 |

| AVERAGE | SD | VC |
|---|---|---|
| 0.25 | 0.003 | 1.2% |

The results indicate that the test is repetitive; the VC is lower than 10%.

| Sample | Dilution | 1 | 2 | 3 | 4 | 5 | 6 | 7 | 8 | 9 | 10 |
|---|---|---|---|---|---|---|---|---|---|---|---|
| 1 | ½ | 0.12 | 0.12 | 0.12 | 0.12 | 0.12 | 0.13 | 0.12 | 0.13 | 0.12 | 0.12 |
|   | ¼ | 0.06 | 0.06 | 0.06 | 0.07 | 0.06 | 0.06 | 0.06 | 0.06 | 0.07 | 0.06 |
|   | ⅛ | 0.03 | 0.03 | 0.04 | 0.03 | 0.03 | 0.03 | 0.03 | 0.04 | 0.03 | 0.03 |
| 2 | ½ | 0.12 | 0.12 | 0.12 | 0.12 | 0.12 | 0.12 | 0.12 | 0.12 | 0.12 | 0.12 |
|   | ¼ | 0.06 | 0.07 | 0.06 | 0.06 | 0.06 | 0.07 | 0.06 | 0.06 | 0.06 | 0.06 |
|   | ⅛ | 0.03 | 0.03 | 0.03 | 0.03 | 0.03 | 0.03 | 0.03 | 0.03 | 0.04 | 0.04 |
| 3 | ½ | 0.12 | 0.12 | 0.13 | 0.12 | 0.12 | 0.12 | 0.12 | 0.12 | 0.12 | 0.12 |
|   | ¼ | 0.06 | 0.06 | 0.06 | 0.06 | 0.06 | 0.06 | 0.06 | 0.06 | 0.06 | 0.06 |
|   | ⅛ | 0.04 | 0.03 | 0.03 | 0.03 | 0.03 | 0.04 | 0.04 | 0.03 | 0.03 | 0.03 |

½ dilution:

| AVERAGE | SD | VC |
|---|---|---|
| 0.121 | 0.003051 | 2.52% |

¼ dilution:

| AVERAGE | SD | VC |
|---|---|---|
| 0.061333 | 0.003457 | 5.63% |

⅛ dilution:

| AVERAGE | SD | VC |
|---|---|---|
| 0.031 | 0.003051 | 9.84% |

We studied de VC for each dilution. The obtained results indicate the repetitivity of the test; each VC was lower than 10%.

2-Inter-Assay Precision

To check the variability mainly due to the technician manipulations, the same batch of product of the invention was titrated in three different days. Every day, all necessary solutions were freshly prepared and the product samples were stored at 4° C. between the first and the last day of the experiment.

In this assay, one batch of the product of the invention (A003A) was titrated in three different days, 3 different samples with 10 replicates per sample.

Results:

| Day | Sample | 1 | 2 | 3 | 4 | 5 | 6 | 7 | 8 | 9 | 10 |
|---|---|---|---|---|---|---|---|---|---|---|---|
| 1 | 1 | 0.25 | 0.25 | 0.25 | 0.26 | 0.25 | 0.25 | 0.24 | 0.25 | 0.25 | 0.25 |
|   | 2 | 0.25 | 0.25 | 0.25 | 0.25 | 0.25 | 0.25 | 0.25 | 0.25 | 0.25 | 0.25 |
|   | 3 | 0.25 | 0.26 | 0.25 | 0.25 | 0.25 | 0.25 | 0.25 | 0.25 | 0.25 | 0.25 |
| 2 | 1 | 0.25 | 0.26 | 0.25 | 0.25 | 0.25 | 0.25 | 0.25 | 0.25 | 0.25 | 0.25 |
|   | 2 | 0.25 | 0.25 | 0.25 | 0.25 | 0.25 | 0.25 | 0.25 | 0.24 | 0.25 | 0.25 |
|   | 3 | 0.25 | 0.25 | 0.25 | 0.25 | 0.24 | 0.25 | 0.25 | 0.25 | 0.25 | 0.25 |
| 3 | 1 | 0.25 | 0.25 | 0.25 | 0.26 | 0.25 | 0.25 | 0.25 | 0.25 | 0.25 | 0.25 |
|   | 2 | 0.24 | 0.25 | 0.25 | 0.25 | 0.25 | 0.25 | 0.25 | 0.24 | 0.25 | 0.25 |
|   | 3 | 0.25 | 0.25 | 0.25 | 0.25 | 0.25 | 0.25 | 0.25 | 0.25 | 0.26 | 0.25 |

| AVERAGE | SD | VC |
|---|---|---|
| 0.25 | 0.003352 | 1.34% |

The obtained results indicate the repetitivity of the test; the VC was lower than 10%.

3-Inter-Batch Precision

To check the variability of the batch production:

In this assay, three batches of the product of the invention (A001A, A002A and A003A), were titrated. Three samples of each batch with 10 replicates per sample.

| Batch | Assay | 1 | 2 | 3 | 4 | 5 | 6 | 7 | 8 | 9 | 10 |
|---|---|---|---|---|---|---|---|---|---|---|---|
| A001A | 1 | 0.25 | 0.25 | 0.25 | 0.26 | 0.25 | 0.25 | 0.25 | 0.25 | 0.25 | 0.25 |
|   | 2 | 0.25 | 0.25 | 0.25 | 0.24 | 0.25 | 0.25 | 0.24 | 0.25 | 0.25 | 0.25 |
|   | 3 | 0.25 | 0.26 | 0.25 | 0.25 | 0.25 | 0.25 | 0.25 | 0.25 | 0.25 | 0.25 |
| A002A | 1 | 0.26 | 0.25 | 0.25 | 0.25 | 0.26 | 0.25 | 0.25 | 0.25 | 0.25 | 0.25 |
|   | 2 | 0.25 | 0.25 | 0.26 | 0.25 | 0.25 | 0.25 | 0.25 | 0.26 | 0.25 | 0.25 |
|   | 3 | 0.25 | 0.26 | 0.25 | 0.25 | 0.24 | 0.25 | 0.25 | 0.25 | 0.26 | 0.25 |
| A003A | 1 | 0.25 | 0.25 | 0.25 | 0.25 | 0.25 | 0.25 | 0.26 | 0.25 | 0.25 | 0.25 |
|   | 2 | 0.24 | 0.26 | 0.25 | 0.25 | 0.25 | 0.26 | 0.25 | 0.24 | 0.25 | 0.25 |
|   | 3 | 0.24 | 0.25 | 0.25 | 0.24 | 0.25 | 0.25 | 0.25 | 0.25 | 0.25 | 0.25 |

| AVERAGE | SD | VC |
|---------|----------|-------|
| 0.25 | 0.004475 | 1.78% |

No significant differences of Kdo activity were observed in intra-assay, inter-assay and temporal assays, with samples of the product of the invention.

EXAMPLE 5

Immunogenicity Test as Adjuvant for Viral Inactivated Vaccine

Field Test

This field test was carried out in order to assess the efficiency of immunostimulant on the inmunitary answer over serum, total and neutralizing antibodies versus Bovine Herpesvirus 1 (BHV-1) or virus of Infectious Bovine Rhinotracheitis (IBR), induced by the immunization with a routinely inactivated vaccination, in serum-negative calves.

Material And Methodology

1. Herd Selection

To select the test herd, previously 120 animals from other 5 herds of milk cattle were tested. Since in these 5 herds there were serum-positive animals, samples were taken from a sixth herd; animals tested were serum-negative and this herd was selected.

Serologies were carried with the ELISA commercial test that detects total antibodies versus the IBR virus.

2. Acting Protocol: Treatment, Vaccination And Sample Collection 2.1. Treatment And Vaccination Test was carried on 22 serum-negative heifers from a milk herd free from the IBR virus. No new animals were let into the herd during the test. Heifers were separated in the following groups:

Group 1.—Thirteen heifers were treated with 5 ml of immunostimulant compound (6 micrograms/mL) in test days 0 & 7 and were vaccinated with 5 ml of registered commercial vaccine which contains inactivated IBR viruses in days 7 & 28. Both products were injected through deep intramuscular shots on the neck.

Group 2.—Six heifers were immunised with the same vaccination dosage and way in days 7 & 28.

Group 3.—Three heifers were the control group; they were not treated or immunised in order to verify that virus did not circulate.

2.2. Sample Collection

A Blood sample of every animal was taken in days 0, 7, 28 & 58 of test period.

3. Detection of Bovine Herpesvirus (BHV-1) Neutralizing Serum Antibodies

I. Bovine Herpesvirus 1 neutralizing antibodies titter was determined by a standard viral neutralization test; it made use of 100 $DI_{50}CT/25$ μl of the Colorado strain on the "Georgia bovine kidney" (GBK), a well established cell line derived from bovine kidney (provide by Prof. Marcelino Álvarez, Dpto. Sanidad Animal, Facultad de Veterinaria, Universidad de León, España) each serum was tested 4 times.

Serums were titrated from pure serum. Serum was mixed with virus (25 μl of diluted serum and 25 μl of viral suspension) and diluted, its titter was found with the Spearman-Kärber method (TRIMMED SPEARMAN-KARBER (TSK) PROGRAM VERSION 1.5, ECOLOGICAL MONITORING RESEARCH DIVISION ENVIRONMENTAL MONITORING SYSTEMS LABORATORY, U.S. ENVIRONMENTAL PROTECTION AGENCY CINCINNATI, OHIO 45268). It is expressed as the reciprocal of the 50%-protecting highest dilution of serum.

II. On the two research groups, the mean logarithm titter was found and it is expressed as the inverse of its anti-logarithm. Serum-conversion is defined as the fourfold increase of antibodies between every two serum collections.

III. To verify the existence of statistically relevant differences between the mean logarithm titters obtained for the treated and non-treated animal groups in different test days, a statistical analysis (Kinskall-Wallis non-parameter test) was carried out with the Windows-environment EpiInfo software.

Results And Discussion

I. No control animal serum-converted during the test.

II. The serum-conversion rate for days 7 & 28 was 92.3% and 83.3% in the groups of treated and non-treated animals respectively, and for days 28 & 58 was 69.2% and 16.7% in the groups of treated and non-treated animals respectively.

In both cases, serum-conversion rate was higher in the treated animals group than in the non-treated animals group; but the difference between those groups was only statistically significant in the serum-conversion rate between days 28 and 58.

III. In day 28 the mean logarithm titter of IBR neutralizing antibodies was 3.50 in the group of animals treated, which was significantly higher than the titter of 2.37 obtained in the group of non-treated animals In day 58 the mean logarithm titter of IBR neutralizing antibodies was 12 in the group of animals treated, which was significantly higher than the titter of 4.8 obtained in the group of non-treated animals.

IBR virus serum antibodies titters obtained in treated animals were 1.5 and 2.5 higher than those of non-treated animals in days 28 and 58, respectively.

Conclusions

1. As shown by the results obtained, the administration of the immunostimulant compound increased significantly the humoral response as neutralizing antibodies and as protection level in vaccinated animals; therefore it played an important role in the implementation of the immunological response induced by vaccination.
2. The application is recommended:
    in association to any immunization patterns applied to bovine cattle, due to its low cost.
    Basically when animals are in stressing situations such as those taking place in fattening areas, because these results do confirm other clinical and productive results found in other field tests carried in food suckling and grazing calves.

EXAMPLE 6

Induction of Macrophage Differentiation

One of the characteristics of immunomodulatory molecules such as Toll-like receptor (TLR) ligands, including LPS from many bacterial species, is their ability to induce a morphological change in macrophage cell liens associated to a decrease in the proliferate activity In order to study this, J774 (clone J774A168) and Raw 264.7 mouse macrophage cell lines were cultured in RPMI 1640 medium (GIBCO, Gran Island, N.Y.) supplemented with 2 mM L-glutamine (Sigma), antibiotics, gentamicin and 5% FCS. For experiments, cells were cultured in RPMI supplemented with 0.5% FCS and different doses of the Immunostimulant compound of the invention or LPS from *E. coli*. The cultures were incubated for 72 hr. at 37° C. and cell proliferation was evaluated by incorporation of (3H) thymidine (New England Nuclear, Boston, Mass.) into DNA during the last 16 h of culture. The cells were pulsed with 1 µCi of (3H) thymidine and harvested in glass fiber filters using an automatic cell harvester. Radioactive incorporation was measured in a liquid scintillation spectrometer. The assay was carried out in triplicate cultures.

The Immunostimulant composition of the invention induces differentiation of J774 cells as shown in FIG. 1 compared with *E. coli* LPS in Raw macrophages. Differentiation of macrophages is usually associated to a decrease in cell proliferation. The immunostimulant composition of the invention induces a dose-dependent inhibition of the differentiation of J774 macrophages. This effect is around 500 less potent than the one observed with LPS from *E. coli* on weight/vol basis in J774 or Raw macrophages.

EXAMPLE 7

Induction of TNF In Macrophages

One of the most sensitive assays to study the activity of TLR ligands is to study TNF cytokine production by microphages or macrophage cell lines. To test this J774 (clone J774A168) and Raw 264.7 (from ATCC TIB-71) mouse macrophage cell lines were cultured in RPMI 1640 medium (GIBCO, Gran Island, N.Y.) supplemented with 2 mM L-glutamine (Sigma), antibiotics, gentamicin and 5% FCS. For experiments, cells were cultured in RPMI supplemented with 0.5% FCS and different doses of the immunostimulant composition of the invention or LPS from *E. coli*. Cultures were incubated at 37° C., 5% CO2 for 24 hr, and the supernatants were harvested. TNF was detected by a two-site sandwich ELISA (Endogen, Woburn, Mass.).

Unstimulated macrophages do not synthesize TNF detectable by ELISA. The immunostimulant composition of the invention at doses 0.1-10 µg/ml induces in a dose response manner significant TNF production reactivity levels up to 4000 µg/ml in J774 macrophages (FIG. 2a) as well in raw cells. The effect of the immunostimulant of the invention although highly significant was around 500 fold less potent than LPS from *E. coli* (FIG. 2b).

In addition, peritoneal macrophages were isolated by peritoneal lavage from BALB/c or C57BI/6, 12 weeks old mice, 4 days after a single peritoneal injection of 10% thioglycolate solution (1 ml; Difco Laboratories). Macrophages from C57BI/6, considered being a strain of mice prone to mount Th1 responses and from Balb/c that in contrast is thought to be skewed to Th2 responses were treated with the immunostimulant composition of the invention. Cells ($1.5 \times 10^6$/well) were left to adhere for 1 h in 12-well flat bottomed plates and covered with fresh RPMI/0.5% FCS in the presence or absence of the indicated amount of LPS (026.B6 *E. coli* serotype, Sigma) or the immunostimulant of the invention. Cultures were incubated at 37° C., 5% CO2 for 24 hr, and the supernatants were harvested. TNF was detected by a two-site sandwich ELISA (Endogen, Woburn, Mass.).

The immunostimulant composition of the invention induces TNF production in macrophages from both Balb/c and C57B16 strains of mice, although with less potency than *E. coli* LPS at equivalent concentrations (FIG. 3). It can be concluded that the immunostimulant of the invention is 500 fold less potent than *E. coli* LPS is inducing TNF on equivalent concentration basis. Thus, the immunostimulant composition of the invention is able to induce immunostimulatory doses of TNF but not excessive doses than can be toxic and are responsible for the endotoxic shock induced by LPS from *E. coli*.

EXAMPLE 8

Induction of IL-12 In Macrophages

IL-12 is a cytokine mainly secreted by macrophages in response to many stimuli including TCR ligands. IL-12 is one of the most important cytokine since IL-12 control T helper (Th) differentiation towards a Th1 phenotype. IL-12 is a 70 kD heterodimer composed of p35/p40 protein chains.

To test this, peritoneal macrophages were isolated by peritoneal lavage from BALB/c or C57BI/6, 12 weeks old mice, 4 days after a single peritoneal injection of 10% thioglycolate solution (1 ml; Difco Laboratories). Cells ($1.5 \times 10^6$/well) were left to adhere for 1 h in 12-well flat bottomed plates and covered with fresh RPMI/0.5% FCS in the presence or absence of the indicated amount of LPS (026. B6 *E. coli* serotype, Sigma) or the immunostimulant composition of the invention. Cultures were incubated at 37° C., 5% $CO_2$ for 24 hr, and the supernatants were harvested. Il-12 was detected by ELISA. The immunostimulant of the invention at doses of 10 mµg/ml induces large amounts of IL-12 in peritoneal macrophages from both C57BI/6 and Balb/c (FIG. 4)

EXAMPLE 9

Induction of IFN-Gamma Production By Spleen Lymphocytes

Spleen cell (SC) suspensions were prepared from mice. SC were depleted of erythrocytes by hypotonic lysis with distilled water and resuspended in RPMI-1640 complete medium containing 5% FCS, 2 mM L-glutamine, penicillin (100 U/ml) and streptomycin (100 ng/ml) (GIBCO Laboratories, Grand Island, N.Y.).

Spleen cells ($0.4 \times 10^6$ cells/well) were cultured in 96-well flat-bottom culture plates (Costar, Cambridge, Mass.) in 250 µl of culture medium (RPMI 1640, 10% FCS, 2 mM L-glutamine, $5 \times 10^{-5}$ M 2-mercaptoethanol, 100 U/ml penicillin, 0.1 µg/ml streptomycin) in an atmosphere of 5% $CO_2$ at 37° C. Cells were activated with Concanavalin A (Con A) (10 ng/ml) in the presence or absence of the indicated amount of the Immunostimulant compound.

Mouse IFN-γ was measured in 24 h supernatants obtained from cultures of spleen cells in the presence or the absence of Con A. They were assayed by specific sandwich ELISA mouse MiniKit (Endogen), according to manufacturer's instructions. As show in FIG. 5, Con A stimulation induces a large amount of IFN-gamma secretion by spleen cells from both strains of mice, suggestive of stimulating a Th1 response characterized by the production of IFN gamma.

EXAMPLE 10

Immunostimulant Act Via TLR4 And TLR2 Receptors

To address the putative receptor used by the immunostimulant of the invention, mouse peritoneal macrophages or spleen cells from deficient in either TLR2 or TLR4 receptor were used in the assays mentioned above.

Peritoneal macrophages were isolated by peritoneal lavage from C57BI/6 or C57BI/6 tlr4−/− or C57BI/6 tlr2−/− (Sarna J R, Dyck R H, Whishaw I Q. 2000. The Dalila effect:

C57BL6 mice barber whiskers by plucking. Behavioral Brain Research, 108 (1):39-45. PubMedID: 10680755) 12 weeks old mice, 4 days after a single peritoneal injection of 10% thioglycolate solution (1 ml; Difco Laboratories). Cells (1.5× 106/well) were left to adhere for 1 h in 12-well flat bottomed plates and covered with fresh RPMI/0.5% FCS in the presence or absence of the indicated amount of LPS (026.B6 *E. coli* serotype, Sigma) or the immunostimulant of the invention. Cultures were incubated at 37° C., 5% CO2 for 24 hr, and the supernatants were harvested. TNF and IL-12 was detected by a two-site sandwich ELISA. The lack of TLR4 in macrophages strongly decreased the ability of the immunostimulant of the invention to induce TNF (FIG. 6) and IL-12 (FIG. 7) whereas TLR-2 deficiency only partially prevents the activity.

Spleen cell (SC) suspensions were prepared from mice. SC were depleted of erytrocytes by hypotonic lysis with distilled water and resuspended in RPMI-1640 complete medium containing 5% FCS, 2 mM L-glutamine, penicillin (100 U/ml) and streptommycin (100 ng/ml) (GIBCO Laboratories, Grand Island, N.Y.).

Spleen cells (0.4×106 cells/well) were cultured in 96-well flat-bottom culture plates (Costar, Cambridge, Mass.) in 250 µl of culture medium (RPMI 1640, 10% FCS, 2 mM L-glutamine, $5\,10^{-5}$ M 2-mercaptoethanol, 100 U/ml penicillin, 0.1 µg/ml streptomycin) in an atmosphere of 5% $CO_2$ at 37° C. Cells were activated with Concanavalin A (10 ng/ml).

Mouse IFN-γ was measured in 24 h supernatants obtained from cultures of spleen cells in the presence or the absence of Con A plus the immunostimulant composition of the invention. They were assayed by specific sandwich ELISA mouse MiniKit (Endogen), according to manufacturer's instructions. As show in FIG. 8, Con A stimulation induces a large amount of IFN-gamma secretion, that were severely depressed in spleen cells from C57Bl/6 tlr2−/− and almost completely disappeared when C57Bl/6 tlr4−/− cell were used.

Thus, the immunostimulant of the invention acts mostly through engaging TLR4 receptors and in part through TLR2.

EXAMPLE 11

T Cells Are Stimulated By *Ochrobactrum Intermedium* LMG 3306 LPS In A Dose-Dependent Manner We study the immune stimulatory capacities of LPS by doing a specific experiment.

B6 C57 mice were infected with 2×105 pfu of Lymphochoremeningitis virus (LCMV) and 7 days later, at the pick of the T cell response induced by the virus, mice were sacrificed, their spleen cells isolated and then subjected to ex vivo stimulation for several hours with different stimuli.

In order to study peptide specific stimulation, spleen cells were incubated for 6 hours in the presence of Brefeldin A (to avoid IFN gamma secretion) with media alone or with the LCMV NP396 peptide, one of the dominant H2b restricted CTL epitopes from LCMV (Denis Hudrisier, Joëlle Riond, and Jean Edouard Gairin, Molecular and Functional Dissection of the H-2D$^b$-Restricted Subdominant Cytotoxic T-Cell Response to Lymphocytic Choriomeningitis Virus, J Virol. 2001 March; 75 (5): 2468-2471)

In order to detect all the activated T cells in the mouse at this time point (independently from the peptide specificity), spleen cells were incubated without and with phorbol myristate acetate (PMA) plus ionomycing at the optimal concentrations.

Finally, and to study the stimulatory capacity of *O. intermedium* LPS, the compound was added at different concentrations: at 0.1 µg/ml, 1 µg/ml, 10 µg/ml and 100 µg/ml.

As shown in FIG. 9, at 0.1 and 1 µg/ml, the stimulation was suboptimal. The maximum level of stimulation was reached at concentrations above 10 µg/ml. At these concentrations, most of the activated CD8 and CD4-T cells scored positive for IFNγ expression, at least compared with the "optimal" protocol of T cell stimulation.

LPS from *Brucella* spp. and *O. anthropi*, which contain lipid A moieties with structural features different from those of *Enterobacteriaceae* elicit biochemical signalling via TLR-4 only at high concentrations (10 µg/ml). Notice that while PMA/ionomycing resulted toxic for both CD8 band CD4 T-cells, LPS was not even at the maximum concentrations used. A big percentage of these cells enter in apoptosis by adding PMA/ionomycing, resulting in much lower numbers of T cells.

The LPS of *O. intermedium* accomplish many of the characteristics to become not only a good adjuvant for more classical uses but also to increase immune responses induced by DNA vaccines.

1. Results obtained in our lab with optimal doses of LPS improve the immune response induced by the DNA plasmids, at least to increase the antibody responses induced in mice.
2. LPS is capable also to both activate virus specific CD8 and CD4 T-cells when added in vitro in a dose-dependent manner.
3. Even when added at 100 µg/ml it results no toxic at all while PMA/ion (commonly used) induces apoptosis to spleen cells.

It is produced by non pathogenic bacteria that it is easy to transform.

The invention claimed is:

1. A method for the treatment of sepsis in a mammalian subject comprising administering to the subject an effective amount of a composition, which comprises an effective amount of Lipopolysaccharide (LPS) from *Ochrobactrum intermedium* LMG3306, optionally in combination with one or more pharmaceutically acceptable excipients.

2. The method according to claim 1, wherein said composition comprises a chemically pure LPS of *Ochrobactrum intermedium* LMG 3306 having a non-solvent component, wherein the non-solvent component is not contaminated with more than 0.2% of other compounds.

3. The method according to claim 2, wherein said composition comprises 0.5-120 µg/ml of LPS from the *Ochrobactrum intermedium* strain LMG3306.

4. The method according to claim 2, wherein the LPS is in a homogeneous suspension in which the micellar phase is stable at 4° C. for more than one year.

* * * * *